US010781193B2

(12) United States Patent
Yasukouchi et al.

(10) Patent No.: US 10,781,193 B2
(45) Date of Patent: Sep. 22, 2020

(54) PROCESS FOR PRODUCING ORGANIC COMPOUND

(71) Applicant: KANEKA CORPORATION, Osaka-shi (JP)

(72) Inventors: Hiroaki Yasukouchi, Takasago (JP); Masaru Mitsuda, Takasago (JP); Akira Nishiyama, Takasago (JP); Makoto Funabashi, Takasago (JP)

(73) Assignee: KANEKA CORPORATION, Osaka-shi (JP)

( * ) Notice: Subject to any disclaimer, the term of this patent is extended or adjusted under 35 U.S.C. 154(b) by 0 days.

(21) Appl. No.: 16/244,824

(22) Filed: Jan. 10, 2019

(65) Prior Publication Data
US 2019/0144404 A1   May 16, 2019

Related U.S. Application Data

(63) Continuation of application No. PCT/JP2017/025219, filed on Jul. 11, 2017.

(30) Foreign Application Priority Data

Jul. 21, 2016 (JP) ................................. 2016-143646

(51) Int. Cl.
| C07D 513/02 | (2006.01) |
| C07D 301/00 | (2006.01) |
| C07C 67/14 | (2006.01) |
| C07C 231/02 | (2006.01) |
| C07D 263/44 | (2006.01) |
| C07C 233/64 | (2006.01) |
| C07D 303/16 | (2006.01) |
| C07D 235/02 | (2006.01) |
| C07C 69/78 | (2006.01) |
| C07D 217/06 | (2006.01) |
| C07D 471/08 | (2006.01) |

(52) U.S. Cl.
CPC ............ *C07D 301/00* (2013.01); *C07C 67/14* (2013.01); *C07C 69/78* (2013.01); *C07C 231/02* (2013.01); *C07C 233/64* (2013.01); *C07D 217/06* (2013.01); *C07D 235/02* (2013.01); *C07D 263/44* (2013.01); *C07D 303/16* (2013.01); *C07D 471/08* (2013.01)

(58) Field of Classification Search
CPC .. C07D 301/00; C07D 217/06; C07D 471/08; C07D 303/16; C07D 263/44; C07D 235/02; C07D 217/02; C07D 487/04; C07D 513/02; C07C 67/14; C07C 231/02; C07C 69/78; C07C 233/64
USPC ........................................................ 546/121
See application file for complete search history.

(56) References Cited

U.S. PATENT DOCUMENTS

| 6,392,079 | B1 | 5/2002 | Silva et al. |
| 2003/0078449 | A1 | 4/2003 | Silva et al. |
| 2005/0065361 | A1 | 3/2005 | Deshmukh et al. |
| 2006/0293535 | A1 | 12/2006 | Davis et al. |
| 2007/0135513 | A1 | 6/2007 | Pogutter et al. |
| 2012/0053350 | A1 | 3/2012 | Mangion et al. |
| 2012/0101292 | A1 | 4/2012 | Hikosaka et al. |
| 2013/0066037 | A1 | 3/2013 | Hikosaka et al. |
| 2015/0210637 | A1 | 7/2015 | Ford et al. |
| 2015/0315145 | A1 | 11/2015 | Hirai et al. |
| 2019/0144404 | A1 | 5/2019 | Yasukouchi et al. |

FOREIGN PATENT DOCUMENTS

| CN | 101245001 A | | 8/2008 |
| CN | 102875544 A | | 1/2013 |
| CN | 103408427 A | | 11/2013 |
| EP | 1 647 551 A1 | | 4/2006 |
| JP | H02-096551 A | | 4/1990 |
| JP | H02-129151 A | | 5/1990 |
| JP | H09-104642 A | * | 4/1997 |
| JP | H09-104642 A | | 4/1997 |
| JP | 2007-512260 A | | 5/2007 |
| JP | 2011-006367 A | | 1/2011 |
| JP | 2012-067030 A | | 4/2012 |
| JP | 2012067030 | * | 4/2012 |
| JP | 2012-087105 A | | 5/2012 |
| JP | 2015-533802 A | | 11/2015 |
| WO | WO 2014/069351 A1 | | 5/2014 |

OTHER PUBLICATIONS

International Search Report dated Oct. 10, 2017, in PCT/JP2017/025219, filed Jul. 11, 2017 (3 pages).
Fuse et al, Continuous in situ generation and reaction of phosgene in a microflow system, Chem.Commun., 2011, 47, 12661-12663.
Fuse et al, Efficient Amide Bond Formation through a Rapid and Strong Activation of Carboxylic Acids in a Microflow Reactor, Angew. Chem. Int. Ed., 2014, 53, 851-855.
Murray G. Rosenberg et al., Inter- and Innermolecular Reactions of Chloro(phenyl)carbine, J. Org. Chem., 2003, 68, 4819-4832.
Joel D. Moore et al., High-Load, ROMP-Generated Oligomeric Bis-acid Chlorides: Design of Soluble and Insoluble Nucleophile Scavengers, Organic Letters, 2003, 5(23), 4241-4244.
Extended European Search Report dated Mar. 13, 2020, in European Patent Application No. 17830896.1.

(Continued)

*Primary Examiner* — Taylor V Oh
(74) *Attorney, Agent, or Firm* — Oblon, McClelland, Maier & Neustadt, L.L.P.

(57) ABSTRACT

The present disclosure provides a reaction of a chlorine-containing compound using a flow reactor which is less restricted by a solvent to be used. In the present disclosure, an organic compound is produced by supplying a reaction substrate having at least one functional group which can react with chlorine and is selected from the group consisting of hydroxy group, a thiol group, an amino group, a carboxyl group, a thiocarboxyl group, and an acid amide group, and a chlorine-containing compound to a flow reactor together with a trialkyl amine having 9 to 40 carbon atoms and an organic solvent, and allowing the reaction substrate and the chlorine-containing compound to react with each other.

14 Claims, No Drawings

(56) References Cited

OTHER PUBLICATIONS

Chen P.-S.: "Pyrolytic chemistry of benzyl benzoate", Journal of the Chinese Chemical Sociey, vol. 41, Apr. 1, 1994, pp. 597-599.

\* cited by examiner

PROCESS FOR PRODUCING ORGANIC COMPOUND

CROSS-REFERENCES TO RELATED APPLICATIONS

This application is a continuation of International Patent Application No. PCT/JP2017/025219, filed on Jul. 11, 2017, and claims priority to Japanese Patent Application No. 2016-143646, filed on Jul. 21, 2016, all of which are incorporated herein by reference in their entireties.

TECHNICAL FIELD

The present invention relates to a process for producing an organic compound using a flow reactor.

BACKGROUND ART

As compared with a batch reactor, a flow reactor enables a reaction in a much smaller space, and therefore can achieve high-speed mixing, precise temperature control, and precise retention time control, and also easily achieves reaction field containment. Accordingly, even a reaction such as "a cryogenic reaction", "a high temperature and high pressure reaction", or "a reaction in which a highly toxic substance is handled" which is regarded as difficult to scale up with a batch reactor can be scaled up with a flow reactor. Moreover, a flow reactor can also be designed as a compact device, so that energy and space can be saved. Selection of a flow reactor can also cut equipment investment. Therefore, many pharmaceutical, agricultural, and chemical manufacturers have considered introducing a flow reactor. Pharmaceuticals, agrochemicals, and key raw materials thereof are often commercially produced using an organic synthesis reaction. For commercially carrying out the above-mentioned reaction regarded as difficult to scale up with a batch reactor, it is meaningful to enable the scale-up with a flow reactor.

PRIOR ART DOCUMENT

Patent Document

Patent Document 1: JP 2011-6367 (A)

Non-Patent Document

Non-Patent Document 1: Fuse et al, Chem. Commun., 2011, 47, 12661-12663
Non-Patent Document 2: Fuse et al, Angew. Chem. Int. Ed., 2014, 53, 851-855

SUMMARY OF THE INVENTION

Problems to be Solved by the Invention

A chlorine-containing compound is used as a reagent for various organic synthesis reactions because of its high reactivity, and is used for, for example, allowing a nucleophilic substitution reaction to occur on carbon atom adjacent to chlorine atom. In particular, a chlorine-containing compound reacts with a compound having a hetero atom such as an alcohol, a thiol, an amine, or a carboxylic acid to form a corresponding ether, sulfide, amine, ester, or the like. In such a reaction, the reaction is often accelerated by using a tertiary amine as a catalyst. However, in a reaction of a chlorine-containing compound with a compound having a hetero atom, hydrogen chloride is generated as a by-product, and the hydrogen chloride binds to the tertiary amine to by-produce an amine hydrochloride. This amine hydrochloride is often a solid, and a solid of the amine hydrochloride precipitates out of a generally often used general-purpose solvent, and thus a reaction system forms slurry. When the reaction is carried out in a batch reactor, such a precipitation is not particularly problematic. In a flow reactor, however, a line is clogged by the solid precipitated in a flow channel, and thus a serious problem such that a reagent cannot be stably fed occurs. That is, a reaction of a chlorine-containing compound in a flow reactor is restricted from the viewpoint of ensuring the solubility of an amine hydrochloride, and for example, it is difficult to freely select an organic solvent. For example, a reaction of a chlorine-containing compound using a flow reactor is described in Patent Document 1, Non-Patent Documents 1, and 2, and the like, however, in any reaction, a solvent to be used is limited from the viewpoint of precipitation of an amine hydrochloride.

To be specific, in Patent Document 1, a divalent phenolic compound and a phosgene compound are allowed to continuously react with each other in a microchannel in the presence of an inert organic solvent, and a hydroxide or an alkali metal carbonate is used as a base. The base is used as an aqueous solution, and a reaction is carried out in an inert organic solvent/water two-phase system by dissolving the divalent phenolic compound in the aqueous solution. An alkali metal hydroxide salt cannot be dissolved in an organic solvent, so that the use of water is essential for the reaction of Patent Document 1 from the viewpoint of ensuring the solubility of the salt.

Non-Patent Document 1 discloses a process for producing an acid amide by allowing an O-benzylserine derivative and phosgene to react with each other in the presence of diisopropylethylamine with a microreactor to produce an acid chloride, and subsequently, allowing the acid chloride to react with benzylamine or diethylamine. Also in Non-Patent Document 2, an acid chloride is produced by allowing an O-benzylserine derivative and phosgene to react with each other in the presence of diisopropylethylamine in the same method as in Non-Patent Document 1, and then, the acid chloride is allowed to react with a phenylalanine ester. Diisopropylethylamine hydrochloride used in the reaction of Non-Patent Documents 1 and 2 has low solubility in many general organic solvents according to the examination by the present inventors. Therefore, in Non-Patent Document 1, dichloromethane which can dissolve even an amine salt having low solubility is used. Also in Non-Patent Document 2, dimethylformamide (DMF) or acetonitrile having a relatively high dissolving ability is used. However, dichloromethane has problems in that it places a heavy burden on the environment and also is toxic to the human body. In addition, solubility or reactivity with dichloromethane is often problematic depending on a reaction substrate. Therefore, it is meaningful to solve the problem of clogging of the line in various reaction solvents. Further, even if a diisopropylethylamine salt can be dissolved in DMF or acetonitrile, the salt precipitates out of an ether solvent such as tetrahydrofuran (THF) or methyl tert-butyl ether (MTBE) or of an ester solvent such as isopropyl acetate according to the examination by the present inventors. That is, the usable solvent is limited to a water-soluble solvent, and there is a restriction, for example, a reaction solution cannot be washed with water. Further, the range of choice of a solvent to be used is small, and therefore, when a reaction using a flow reactor is applied to part of the steps of producing a final product through a plurality of steps, it is difficult to adjust the solvent to a solvent used in the previous step or the post step. Thus, the cost increase because of the necessity to substitute the solvent.

Accordingly, an object of the present invention is to provide a reaction of a chlorine-containing compound using a flow reactor which is less restricted by a solvent to be used.

Solutions to the Problems

As a result of intensive studies for achieving the above object, the inventors have found that when a trialkyl amine having 9 to 40 carbon atoms is used as a tertiary amine, a by-produced amine hydrochloride solid does not precipitate out of most solvents, thereby avoiding the problem of clogging of a line in a flow reactor and also succeeding in maintaining the reactivity. The invention has been made based on such finding.

That is, the present invention is as follows.

[1] A process for producing an organic compound, comprising:
supplying a reaction substrate having at least one functional group which can react with chlorine and is selected from the group consisting of hydroxy group, a thiol group, an amino group, a carboxyl group, a thiocarboxyl group, and an acid amide group, and a chlorine-containing compound to a flow reactor together with a trialkyl amine having 9 to 40 carbon atoms and an organic solvent, and
allowing the reaction substrate and the chlorine-containing compound to react with each other.

[2] The process according to [1], wherein
the flow reactor has two or more raw material feeding ports, a mixing unit to mix a fed raw material, and a reactor unit in which a mixed solution flows, and
an organic solvent solution in which the reaction substrate and the trialkyl amine are dissolved, and an organic solvent solution in which the chlorine-containing compound is dissolved are separately fed to the reactor unit from the raw material feeding ports.

[3] The process according to [1] or [2], wherein the organic solvent is at least one selected from an aliphatic hydrocarbon solvent, an aromatic hydrocarbon solvent, an ether solvent, an ester solvent, a ketone solvent, a nitrile solvent, and an amide solvent.

[4] The process according to any one of [1] to [3], wherein an amount of the trialkyl amine is 3 parts by weight or more with respect to 100 parts by weight of the solvent.

[5] The process according to any one of [1] to [4], wherein the trialkyl amine is tripropylamine, tributylamine, trihexylamine, or trioctylamine.

[6] The process according to any one of [1] to [5], wherein the reaction substrate is at least one selected from compounds represented by the following formulae (a1) to (a3):

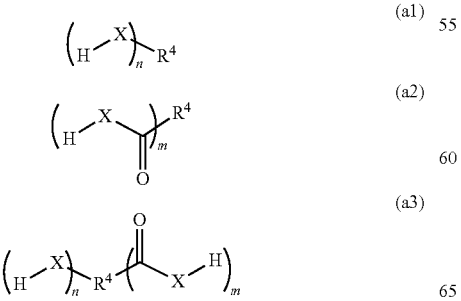

wherein $R^4$ represents a portion other than the functional group of the reaction substrate; X represents O, S, or $NR^5$; $R^5$ represents hydrogen atom, an alkyl group having 1 to 20 carbon atoms and optionally having a substituent, an alkenyl group having 2 to 20 carbon atoms and optionally having a substituent, a cycloalkyl group having 3 to 20 carbon atoms and optionally having a substituent, an aralkyl group having 7 to 20 carbon atoms and optionally having a substituent, an aryl group having 6 to 20 carbon atoms and optionally having a substituent, a heteroaryl group having 3 to 20 carbon atoms and optionally having a substituent, an alkoxy group having 1 to 20 carbon atoms and optionally having a substituent, an aralkyloxy group having 7 to 20 carbon atoms and optionally having a substituent, or an aryloxy group having 6 to 20 carbon atoms and optionally having a substituent; $R^4$ and $R^5$ may be bonded to each other; when a plurality of X's are present, X's may be the same or different; and n and m each represent an integer of 1 to 3, the chlorine-containing compound is at least one selected from compounds represented by the following formulae (1) to (8) and synthetic equivalents thereof:

(1)

(2)

(3)

(4)

(5)

(6)

(7)

(8)

wherein $R^1$, $R^2$, and $R^3$ may be the same or different, and each represent an alkyl group having 1 to 20 carbon atoms and optionally having a substituent, an alkenyl group having 2 to 20 carbon atoms and optionally having a substituent, a cycloalkyl group having 3 to 20 carbon atoms and optionally having a substituent, an aralkyl group having 7 to 20 carbon atoms and optionally having a substituent, an aryl group having 6 to 20 carbon atoms and optionally having a substituent, or a heteroaryl group having 3 to 20 carbon atoms and optionally having a substituent; and $R^1$ and $R^2$, $R^1$ and $R^3$, and $R^2$ and $R^3$ may be bonded to each other, and the organic compound obtained by reacting the reaction substrate and the chlorine-containing compound is at least one selected from compounds represented by the following formulae (9) to (34):

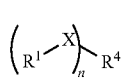 (9)

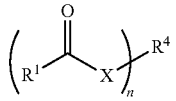 (10)

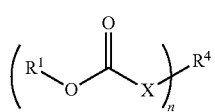 (11)

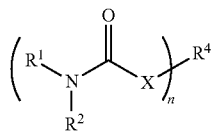 (12)

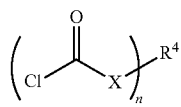 (13)

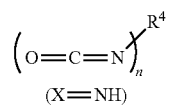 (14)

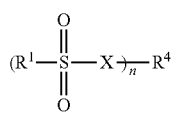 (15)

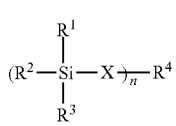 (16)

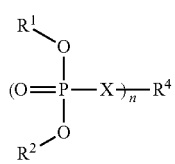 (17)

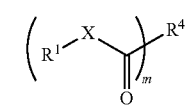 (18)

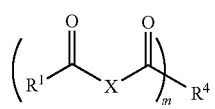 (19)

-continued

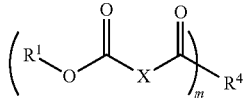 (20)

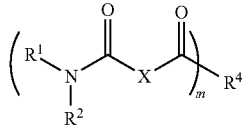 (21)

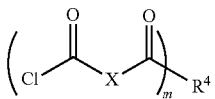 (22)

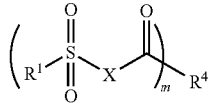 (23)

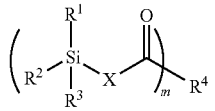 (24)

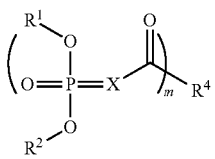 (25)

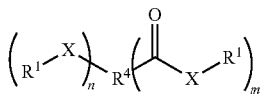 (26)

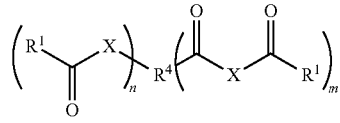 (27)

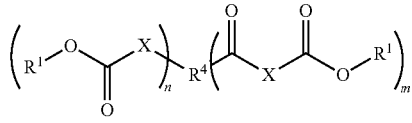 (28)

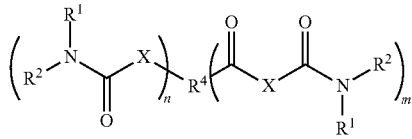 (29)

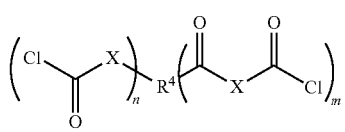 (30)

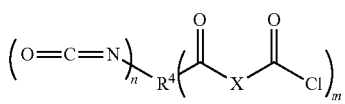 (31)

-continued

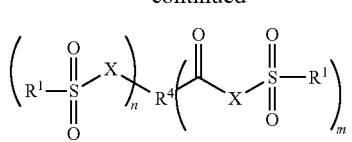

(32)

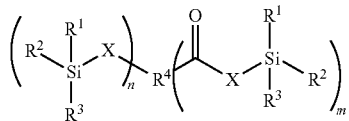

(33)

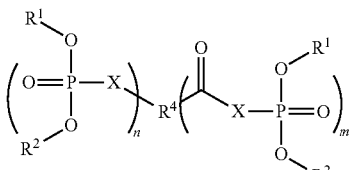

(34)

wherein $R^1$ to $R^4$, X, n, and m are the same as above.

[7] The process according to [6], wherein $R^4$ represents an alkyl group having 1 to 20 carbon atoms and optionally having a substituent or a divalent or trivalent group obtained by removing one or two hydrogen atoms from the alkyl group; an alkenyl group having 2 to 20 carbon atoms and optionally having a substituent or a divalent or trivalent group obtained by removing one or two hydrogen atoms from the alkenyl group; a cycloalkyl group having 3 to 20 carbon atoms and optionally having a substituent or a divalent or trivalent group obtained by removing one or two hydrogen atoms from the cycloalkyl group; an aralkyl group having 7 to 20 carbon atoms and optionally having a substituent or a divalent or trivalent group obtained by removing one or two hydrogen atoms from the aralkyl group; an aryl group having 6 to 20 carbon atoms and optionally having a substituent or a divalent or trivalent group obtained by removing one or two hydrogen atoms from the aryl group; or a heteroaryl group having 3 to 20 carbon atoms and optionally having a substituent or a divalent or trivalent group obtained by removing one or two hydrogen atoms from the heteroaryl group, X represents O, S, or $NR^5$, wherein $R^5$ represents hydrogen atom, an alkyl group having 1 to 20 carbon atoms and optionally having a substituent, an alkenyl group having 2 to 20 carbon atoms and optionally having a substituent, a cycloalkyl group having 3 to 20 carbon atoms and optionally having a substituent, an aralkyl group having 7 to 20 carbon atoms and optionally having a substituent, an aryl group having 6 to 20 carbon atoms and optionally having a substituent, a heteroaryl group having 3 to 20 carbon atoms and optionally having a substituent, an alkoxy group having 1 to 20 carbon atoms and optionally having a substituent, an aralkyloxy group having 7 to 20 carbon atoms and optionally having a substituent, or an aryloxy group having 6 to 20 carbon atoms and optionally having a substituent, and $R^4$ and $R^5$ may be bonded to each other.

[8] The process according to [6], wherein the reaction substrate is (2R,3R)-3-(2,4-difluorophenyl)-3,4-epoxy-2-butyl alcohol, the chlorine-containing compound is a sulfonyl chloride compound, and the organic compound obtained by reacting the reaction substrate and the chlorine-containing compound is (2R,3R)-3-(2,4-difluorophenyl)-3,4-epoxy-2-butylsulfonate.

[9] The process according to [6], wherein the reaction substrate is (S)-1-phenyl-1,2,3,4-tetrahydroisoquinoline, the chlorine-containing compound is phosgene (5) or a synthetic equivalent thereof, and the organic compound obtained by reacting the reaction substrate and the chlorine-containing compound is (S)-1-phenyl-1,2,3,4-tetrahydroisoquinolin-ecarbonyl chloride.

[10] The process according to any one of [1] to [5], wherein the reaction substrate is at least one selected from compounds represented by the following formulae (a4) to (a6):

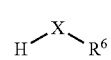

(a4)

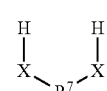

(a5)

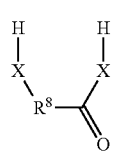

(a6)

wherein $R^6$, $R^7$, and $R^8$ each represent a portion other than the functional group of the reaction substrate; X represents O, S, or $NR^5$; $R^5$ represents hydrogen atom, an alkyl group having 1 to 20 carbon atoms and optionally having a substituent, an alkenyl group having 2 to 20 carbon atoms and optionally having a substituent, a cycloalkyl group having 3 to 20 carbon atoms and optionally having a substituent, an aralkyl group having 7 to 20 carbon atoms and optionally having a substituent, an aryl group having 6 to 20 carbon atoms and optionally having a substituent, a heteroaryl group having 3 to 20 carbon atoms and optionally having a substituent, an alkoxy group having 1 to 20 carbon atoms and optionally having a substituent, an aralkyloxy group having 7 to 20 carbon atoms and optionally having a substituent, or an aryloxy group having 6 to 20 carbon atoms and optionally having a substituent; when a plurality of X's are present, X's may be the same or different, the chlorine-containing compound is phosgene or a synthetic equivalent thereof, and the organic compound obtained by reacting the reaction substrate and the chlorine-containing compound is at least one selected from compounds represented by the following formulae (35) to (37):

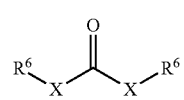

(35)

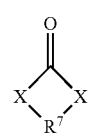

(36)

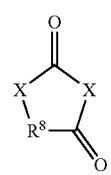

(37)

wherein $R^6$ to $R^8$, and X are the same as above.

[11] The process according to [10], wherein $R^6$ represents an alkyl group having 1 to 20 carbon atoms and optionally having a substituent, an alkenyl group having 2 to 20 carbon atoms and optionally having a substituent, a cycloalkyl group having 3 to 20 carbon atoms and optionally having a substituent, an aralkyl group having 7 to 20 carbon atoms and optionally having a substituent, an aryl group having 6 to 20 carbon atoms and optionally having a substituent, or a heteroaryl group having 3 to 20 carbon atoms and optionally having a substituent, $R^7$ and $R^8$ each represent an alkylene group having 1 to 10 carbon atoms and optionally having a substituent, X represents O, S, or $NR^5$; $R^5$ represents hydrogen atom, an alkyl group having 1 to 20 carbon atoms and optionally having a substituent, an alkenyl group having 2 to 20 carbon atoms and optionally having a substituent, a cycloalkyl group having 3 to 20 carbon atoms and optionally having a substituent, an aralkyl group having 7 to 20 carbon atoms and optionally having a substituent, an aryl group having 6 to 20 carbon atoms and optionally having a substituent, a heteroaryl group having 3 to 20 carbon atoms and optionally having a substituent, an alkoxy group having 1 to 20 carbon atoms and optionally having a substituent, an aralkyloxy group having 7 to 20 carbon atoms and optionally having a substituent, or an aryloxy group having 6 to 20 carbon atoms and optionally having a substituent, and $R^5$ and $R^6$ may be bonded to each other.

[12] The process according to [10], wherein the reaction substrate is N-[1-(S)-ethoxycarbonyl-3-phenylpropyl]-L-alanine, benzyl 4-[({(2S,5R)-5-[(benzyloxy)amino]piperidin-2-yl}carbonyl)amino]piperidine-1-carboxylate, tert-butyl 4-[({(2S,5R)-5-[(benzyloxy)amino]piperidin-2-yl}carbonyl)amino]piperidine-1-carboxylate, benzyl (2S,5R)-5-benzyloxyamino-piperidine-2-carboxylate, methyl (2S,5R)-5-benzyloxyamino-piperidine-2-carboxylate, or (2S,5R)-5-benzyloxyamino-piperidine-2-carboxamide, the chlorine-containing compound is phosgene or triphosgene, and the organic compound obtained by reacting the reaction substrate and the chlorine-containing compound is N-[1-(S)-ethoxycarbonyl-3-phenylpropyl]-L-alanyl-N-carboxylic acid anhydride, benzyl 4-({[(2S,5R)-6-(benzyloxy)-7-oxo-1,6-diazabicyclo[3.2.1.]oct-2-yl]carbamoyl}amino)piperidine-1-carboxylate, tert-butyl 4-({[(2S,5R)-6-(benzyloxy)-7-oxo-1,6-diazabicyclo[3.2.1.]oct-2-yl]carbamoyl}amino) piperidine-1-carboxylate, benzyl (4R,6S)-3-(benzyloxy)-2-oxo-1,3-diazabicyclo[2,2,1]heptane-6-carboxylate, methyl (4R,6S)-3-(benzyloxy)-2-oxo-1,3-diazabicyclo[2,2,1]heptane-6-carboxylate, or (4R,6S)-3-(benzyloxy)-2-oxo-1,3-diazabicyclo[2,2,1]heptane-6-carboxamide.

Effect of the Invention

According to the present invention, a serious problem in the production such that when various organic compounds are produced in a flow reactor using a chlorine-containing compound, a hydrochloride derived from a tertiary amine added as a catalyst precipitates out of a system and a line is occluded can be avoided regardless of a solvent.

MODE FOR CARRYING OUT THE INVENTION

The present invention is characterized in that a process for producing an organic compound (hereinafter sometimes referred to as "product") by reacting a reaction substrate having at least one functional group which can react with chlorine (hereinafter sometimes referred to as "chlorine reactive group") and a chlorine-containing compound in the presence of an amine is carried out using a flow reactor.

Examples of the chlorine reactive group of the reaction substrate include hydroxy group, a thiol group, an amino group, a carboxyl group, a thiocarboxyl group, and an acid amide group. When the reaction substrate has two or more chlorine reactive groups, the chlorine reactive groups may be the same or different. When the reaction substrate has two or more chlorine reactive groups, one group is preferably an amino group, and the rest are preferably selected from an amino group and a carboxyl group.

The reaction substrate can be represented by, for example, the following formulae (a1), (a2), and (a3).

(a1)

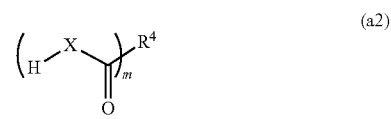

(a2)

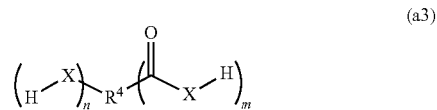

(a3)

Here, $R^4$ represents a portion other than the chlorine reactive group of the reaction substrate. n and m each represent an integer of 1 to 3. n and m are each preferably 1 to 2, and more preferably 1.

In the above formulae, —XH or —C(=O)XH corresponds to the chlorine reactive group. Therefore, X represents O, S, or $NR^5$, and $R^5$ preferably represents hydrogen atom, an alkyl group having 1 to 20 carbon atoms and optionally having a substituent, an alkenyl group having 2 to 20 carbon atoms and optionally having a substituent, a cycloalkyl group having 3 to 20 carbon atoms and optionally having a substituent, an aralkyl group having 7 to 20 carbon atoms and optionally having a substituent, an aryl group having 6 to 20 carbon atoms and optionally having a substituent, a heteroaryl group having 3 to 20 carbon atoms and optionally having a substituent, an alkoxy group having 1 to 20 carbon atoms and optionally having a substituent, an aralkyloxy group having 7 to 20 carbon atoms and optionally having a substituent, or an aryloxy group having 6 to 20 carbon atoms and optionally having a substituent. Incidentally, $R^5$ may be bonded to $R^4$. When a plurality of X's are present, X's may be the same or different.

The alkyl group serving as $R^5$ of $NR^5$ is preferably a group having 1 to 10 carbon atoms such as a methyl group, an ethyl group, a propyl group, a butyl group, a pentyl group, or a hexyl group, and more preferably a group having 1 to 4 carbon atoms.

The alkenyl group serving as $R^5$ of $NR^5$ is preferably a group having 2 to 10 carbon atoms such as an ethenyl group, a propenyl group, a butenyl group, a pentenyl group, or a hexenyl group, and more preferably a group having 2 to 4 carbon atoms.

The cycloalkyl group serving as $R^5$ of $NR^5$ is preferably a group having 3 to 10 carbon atoms such as a cyclopropyl group, a cyclobutyl group, a cyclopentyl group, or a cyclohexyl group, and more preferably a group having 5 to 6 carbon atoms.

The aralkyl group serving as $R^5$ of $NR^5$ is preferably a group having 7 to 15 carbon atoms such as a benzyl group, a phenethyl group, or a phenylpropyl group, and more preferably a group having 7 to 10 carbon atoms.

The aryl group serving as $R^5$ of $NR^5$ is preferably a group having 6 to 10 carbon atoms such as a phenyl group, a toluyl group, or a naphthyl group, and more preferably a group having 6 to 8 carbon atoms.

Examples of the heteroaryl group serving as $R^5$ of $NR^5$ include a pyridinyl group, a pyrazinyl group, a pyrimidinyl group, and a pyridazinyl group.

The alkoxy group serving as $R^5$ of $NR^5$ is preferably a group having 1 to 10 carbon atoms such as a methoxy group, an ethoxy group, a propoxy group, or a butoxy group, and more preferably a group having 1 to 4 carbon atoms.

The aralkyloxy group serving as $R^5$ of $NR^5$ is preferably a group having 7 to 15 carbon atoms such as a benzyloxy group or a phenethyloxy group, and more preferably a group having 7 to 10 carbon atoms.

The aryloxy group serving as $R^5$ of $NR^5$ is preferably a group having 6 to 10 carbon atoms such as a phenyloxy group or a naphthyloxy group, and more preferably a group having 6 to 8 carbon atoms.

Examples of the substituent that $R^5$ may have include fluorine atom; an alkoxy group such as a methoxy group, an ethoxy group, a phenoxy group, or a benzyloxy group; a cyclic ether group such as an epoxy group; an alkylthio group such as a methylthio group; a trifluoromethyl group; an acetyl group; a benzoyl group; a cyano group; a nitro group; an alkoxycarbonyl group such as a methoxycarbonyl group or an ethoxycarbonyl group; a dialkylamino group such as a dimethylamino group, a diethylamino group, or a pyrrolidyl group; and a protected amino group such as a benzyloxycarbonylamino group, a tert-butylcarbonylamino group, an acetylamino group, or a benzoylamino group. Further, the substituent may be a divalent group, and includes, for example, —$CH_2$—O—. When two bonds of —$CH_2$—O— are bonded to the same carbon atom, an oxirane ring is formed. There is no restriction on the number of substituents.

$R^4$ can have various complicated structures according to the reaction substrate, but may have a simple structure. When the reaction substrate is a substrate having a simple structure, examples of $R^4$ include an alkyl group having 1 to 20 carbon atoms and optionally having a substituent or a divalent or trivalent group obtained by removing one or two hydrogen atoms from the alkyl group; an alkenyl group having 2 to 20 carbon atoms and optionally having a substituent or a divalent or trivalent group obtained by removing one or two hydrogen atoms from the alkenyl group; a cycloalkyl group having 3 to 20 carbon atoms and optionally having a substituent or a divalent or trivalent group obtained by removing one or two hydrogen atoms from the cycloalkyl group; an aralkyl group having 7 to 20 carbon atoms and optionally having a substituent or a divalent or trivalent group obtained by removing one or two hydrogen atoms from the aralkyl group; an aryl group having 6 to 20 carbon atoms and optionally having a substituent or a divalent or trivalent group obtained by removing one or two hydrogen atoms from the aryl group; and a heteroaryl group having 3 to 20 carbon atoms and optionally having a substituent or a divalent or trivalent group obtained by removing one or two hydrogen atoms from the heteroaryl group.

Examples of the alkyl group, the alkenyl group, the cycloalkyl group, the aralkyl group, the aryl group, and the heteroaryl group as $R^4$ include the same groups as those exemplified for $R^5$. Further, examples of the substituent of $R^4$ include the same groups as those exemplified for the substituent of $R^5$.

$R^5$ and $R^4$ are bonded to each other to form a ring containing at least one or more (preferably 5 or less, more preferably 2 or less) nitrogen atoms as the constituent elements of the ring. The ring formed by bonding $R^5$ and $R^4$ to each other has preferably 2 or more, more preferably 4 or more, preferably 30 or less, and more preferably 20 or less carbon atoms. The ring formed by bonding $R^5$ and $R^4$ to each other is preferably a monocyclic system, a bicyclic system, or a tricyclic system.

The ring formed by bonding $R^5$ and $R^4$ to each other may have a substituent, and examples of the substituent include an alkyl group having 1 to 20 carbon atoms and optionally having a substituent, an alkenyl group having 2 to 20 carbon atoms and optionally having a substituent, a cycloalkyl group having 3 to 20 carbon atoms and optionally having a substituent, an aralkyl group having 7 to 20 carbon atoms and optionally having a substituent, an aryl group having 6 to 20 carbon atoms and optionally having a substituent, a heteroaryl group having 3 to 20 carbon atoms and optionally having a substituent, an alkoxy group having 1 to 20 carbon atoms and optionally having a substituent, an aralkyloxy group having 7 to 20 carbon atoms and optionally having a substituent, an aryloxy group having 6 to 20 carbon atoms and optionally having a substituent, and a substituent that the group as $R^5$ may have. The substituent is preferably an aryl group having 6 to 20 carbon atoms and optionally having a substituent, and a specific group can appropriately refer to $R^5$. The number of substituents is not particularly limited.

When the reaction substrate has "X—$R^4$" in the structural formula as in the formula (a1) or (a3), $R^5$ and $R^4$ are bonded to each other to form a ring containing at least one or more (preferably 5 or less, more preferably 2 or less) nitrogen atoms as the constituent elements of the ring. Examples of the ring forming H—$NR^5$—$R^4$ by bonding $R^5$ and $R^4$ to each other include the following rings.

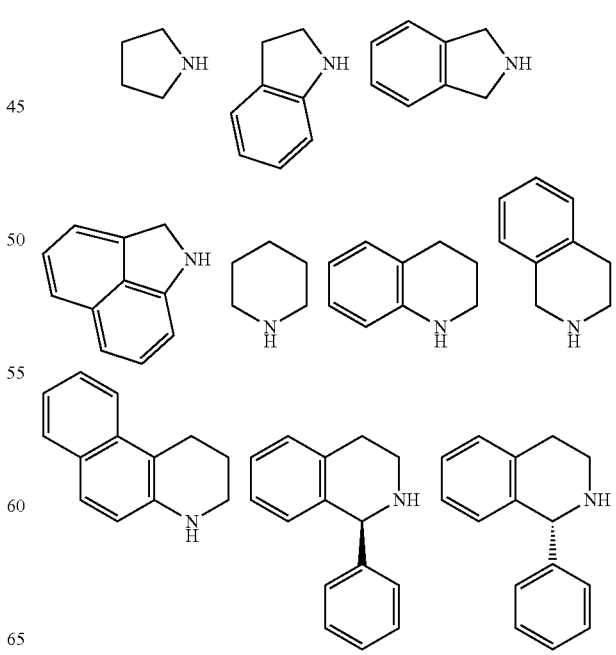

On the other hand, when the reaction substrate has "X—C(═O)—R⁴" in the structural formula as in the formula (a2) or (a3), R⁵ and R⁴ are bonded to each other to form a ring containing >C(═O) and at least one or more (preferably 5 or less, more preferably 2 or less) nitrogen atoms as the constituent elements of the ring. Examples of the ring forming H—NR⁵—C(═O)—R⁴ by bonding R⁵ and R⁴ to each other include the following rings.

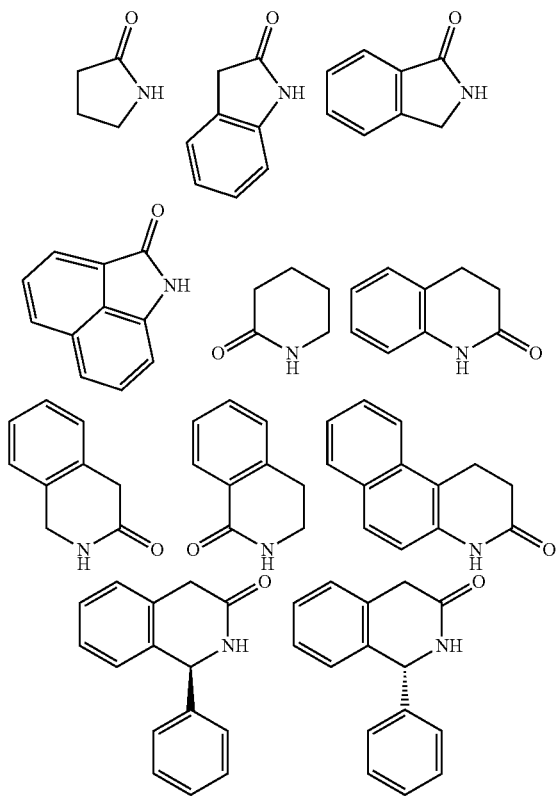

The reaction substrates (a1) to (a3) can be represented by, for example, the following formulae (a4) to (a6) in one embodiment.

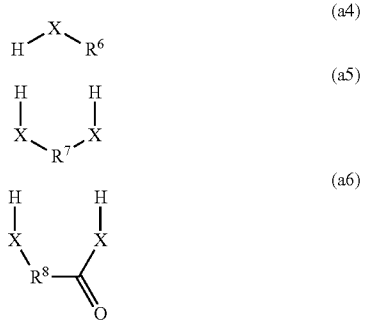

(In the formulae, R⁶, R⁷, and R⁸ each represent a portion other than the chlorine reactive functional group of the reaction substrate, and X is the same as described above. When a plurality of X's are present, X's may be the same or different.)

R⁶ to R⁸ can also have various complicated structures according to the reaction substrate as with R⁴, but may have a simple structure. When the reaction substrate is a substrate having a simple structure, examples of R⁶ include an alkyl group having 1 to 20 carbon atoms and optionally having a substituent, an alkenyl group having 2 to 20 carbon atoms and optionally having a substituent, a cycloalkyl group having 3 to 20 carbon atoms and optionally having a substituent, an aralkyl group having 7 to 20 carbon atoms and optionally having a substituent, an aryl group having 6 to 20 carbon atoms and optionally having a substituent, and a heteroaryl group having 3 to 20 carbon atoms and optionally having a substituent. Examples of the alkyl group, the alkenyl group, the cycloalkyl group, the aralkyl group, the aryl group, and the heteroaryl group as R⁶ include the same groups as those exemplified for R⁵. Further, examples of the substituent of R⁶ include the same groups as those exemplified for the substituent of R⁵.

When X represents NR⁵, R⁵ and R⁶ may be bonded to each other. When R⁵ and R⁶ are bonded to each other, a ring containing a nitrogen atom as a constituent element is formed. Examples of the ring include the same rings as the rings formed by bonding R⁵ and R⁴ to each other. That is, examples of the ring formed by bonding R⁵ and R⁶ to each other include the same rings as in the case of having "X—R⁴" in the structural formula.

When the reaction substrate is a substrate having a simple structure, R⁷ and R⁸ are each preferably an alkylene group having 1 to 10 carbon atoms and optionally having a substituent; a cycloalkanediyl group having 4 to 10 carbon atoms and optionally having a substituent (particularly, a cycloalkane-1,2-diyl group) such as a cyclopentane-1,2-diyl group or a cyclohexane-1,2-diyl group; or a divalent aromatic hydrocarbon group having 6 to 10 carbon atoms and optionally having a substituent such as a benzene-1,2-diyl group. The alkylene group is more preferably a group having 1 to 6 carbon atoms such as a methylene group, an ethylene group, a propylene group, a butanediyl group, a pentanediyl group, or a hexanediyl group, and still more preferably a group having 1 to 3 carbon atoms. Examples of the substituent of R⁷ and R⁸ also include the same groups as those exemplified for the substituent of R⁵.

The reaction substrate having a complicated structure among the preferred reaction substrates includes N-[1-(S)-ethoxycarbonyl-3-phenylpropyl]-L-alanine, benzyl 4-[({(2S,5R)-5-[(benzyloxy)amino]piperidin-2-yl}carbonyl)amino]piperidine-1-carboxylate, tert-butyl 4-[({(2S,5R)-5-[(benzyloxy)amino]piperidin-2-yl}carbonyl)amino]piperidine-1-carboxylate, benzyl (2S,5R)-5-benzyloxyamino-piperidine-2-carboxylate, methyl (2S,5R)-5-benzyloxyamino-piperidine-2-carboxylate, and (2S,5R)-5-benzyloxyamino-piperidine-2-carboxamide. The reaction substrate having a simple structure among the preferred reaction substrates includes methanol, ethanol, benzyl alcohol, phenol, (2R,3R)-3-(2,4-difluorophenyl)-3,4-epoxy-2-butyl alcohol, benzenethiol, benzylamine, (R)-1-phenylethylamine, (S)-1-phenyl-1,2,3,4-tetrahydroisoquinoline, aniline, acetic acid, benzoic acid, thioacetic acid, thiobenzoic acid, and acetamide.

The reaction substrate is particularly preferably N-[1-(S)-ethoxycarbonyl-3-phenylpropyl]-L-alanine, benzyl 4-[({(2S,5R)-5-[(benzyloxy)amino]piperidin-2-yl}carbonyl)amino]piperidine-1-carboxylate, tert-butyl 4-[({(2S,5R)-5-[(benzyloxy)amino]piperidin-2-yl}carbonyl)amino]piperidine-1-carboxylate, benzyl (2S,5R)-5-benzyloxyamino-piperidine-2-carboxylate, methyl (2S,5R)-5-benzyloxyamino-piperidine-2-carboxylate, (2S,5R)-5-benzyloxyamino-piperidine-2-carboxamide, (2R,3R)-3-(2,4-difluorophenyl)-3,4-epoxy-2-butyl alcohol, or (S)-1-phenyl-1,2,3,4-tetrahydroisoquinoline, and most preferably N-[1-(S)-ethoxycarbonyl-3-phenylpropyl]-L-alanine, benzyl 4-[({(2S,5R)-5-[(benzyloxy)amino]piperidin-2-yl}carbonyl)amino]piperidine-1-carboxylate, (2R,3R)-3-(2,4-difluorophenyl)-3,4-epoxy-2-butyl alcohol, or (S)-1-phenyl-1,2,3,4-tetrahydroisoquinoline.

The chlorine-containing compound which can react with the reaction substrate includes a compound having a carbon (particularly, carbon having only a σ-bond)-chlorine bond; a compound having a silicon-chlorine bond; a compound having an acid chloride structure such as a carboxylic acid chloride, a carbonic acid monoester chloride, a carbonic acid dichloride (phosgene), an N,N-disubstituted carbamoyl chloride, a sulfonic acid chloride, and a phosphoric acid diester chloride; and a synthetic equivalent thereof such as triphosgene which is a phosgene synthetic equivalent. Specifically, for example, a chloride (1) represented by the following formula (1), an acid chloride (2) represented by the following formula (2), a chlorocarbonate ester (3) represented by the following formula (3), a carbamoyl chloride (4) represented by the following formula (4), phosgene (5) represented by the following formula (5), a sulfonyl chloride (6) represented by the following formula (6), a silyl chloride (7) represented by the following formula (7), and a chlorophosphate (8) represented by the following formula (8) are exemplified. The chlorine-containing compounds may be used alone or in combination two or more kinds, and the compounds are generally used alone.

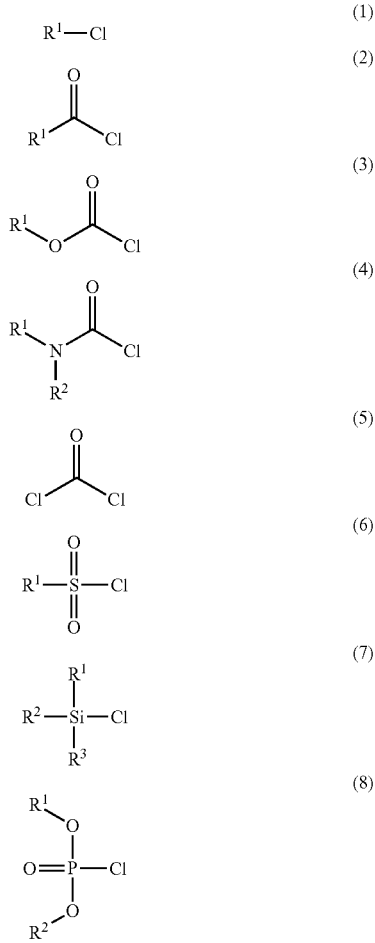

Here, in the formulae, $R^1$, $R^2$, and $R^3$ may be the same or different, and each represent an alkyl group having 1 to 20 carbon atoms and optionally having a substituent, an alkenyl group having 2 to 20 carbon atoms and optionally having a substituent, a cycloalkyl group having 3 to 20 carbon atoms and optionally having a substituent, an aralkyl group having 7 to 20 carbon atoms and optionally having a substituent, an aryl group having 6 to 20 carbon atoms and optionally having a substituent, or a heteroaryl group having 3 to 20 carbon atoms and optionally having a substituent. $R^1$ and $R^2$, $R^1$ and $R^3$, and $R^2$ and $R^3$ may be bonded to each other.

Examples of the alkyl group, the alkenyl group, the cycloalkyl group, the aralkyl group, the aryl group, and the heteroaryl group as $R^1$ to $R^3$ include the same groups as those exemplified for $R^5$. Further, examples of the substituent of $R^1$ to $R^3$ include the same groups as those exemplified for the substituent of $R^5$.

As the chlorine-containing compound, specifically, a chloride such as methyl chloride, ethyl chloride, butyl chloride, benzyl chloride, p-methylbenzyl chloride, p-methoxybenzyl chloride, p-nitrobenzyl chloride, allyl chloride, and triphenylmethyl chloride; an acid chloride such as acetyl chloride, cyclopropanecarbonyl chloride, cyclohexanecarbonyl chloride, and benzoyl chloride; a chlorocarbonate ester such as methyl chlorocarbonate, ethyl chlorocarbonate, isopropyl chlorocarbonate, allyl chlorocarbonate, benzyl chlorocarbonate, phenyl chlorocarbonate, and 9-fluorenylmethyl chlorocarbonate; a carbamoyl chloride such as N,N-dimethylcarbamoyl chloride, N,N-diethylcarbamoyl chloride, and pyrrolidinecarbonyl chloride; phosgene; a sulfonyl chloride such as methanesulfonyl chloride, cyclopropanesulfonyl chloride, p-toluenesulfonyl chloride, and p-nitrobenzenesulfonyl chloride; a silyl chloride such as trimethylsilyl chloride, tert-butyldimethylsilyl chloride, and triphenylsilyl chloride; and a chlorophosphate such as diethylchlorophosphate and diphenylchlorophosphate can be exemplified. The chlorine-containing compound is more preferably benzyl chloride, acetyl chloride, benzoyl chloride, methyl chlorocarbonate, ethyl chlorocarbonate, isopropyl chlorocarbonate, allyl chlorocarbonate, benzyl chlorocarbonate, phenyl chlorocarbonate, 9-fluorenylmethyl chlorocarbonate, phosgene, methanesulfonyl chloride, and p-toluenesulfonyl chloride, and particularly preferably benzoyl chloride, phosgene, and methanesulfonyl chloride. Since the reaction using a flow reactor has a high sealing performance, even a reaction using a highly toxic compound such as phosgene or a synthetic equivalent thereof (triphosgene) can be relatively safely carried out.

The using amount of the chlorine-containing compound is suitably determined by the amount of chlorine in the compound, and preferably determined by the amount of chlorine forming a portion of the structure represented by the formula (1) to the formula (8). The amount of chlorine in the compound is, for example, 0.1 mol or more, preferably 0.3 mol or more, more preferably 0.5 mol or more, and particularly preferably 0.7 mol or more, and is, for example, 15 mol or less, preferably 10 mol or less, more preferably 5 mol or less, and particularly preferably 3 mol or less, relative to 1 mol of the chlorine reactive group in the reaction substrate. The using amount of the synthetic equivalent such as triphosgene is determined in terms of a chlorine-containing compound having an equivalent relationship with the synthetic equivalent. For example, one-third mole of triphosgene corresponds to one mole of phosgene, and the amount of use is determined based on the standard mentioned above.

A product is obtained by reacting substrate and the chlorine-containing compound. Various products are exemplified according to the combination of the reaction substrate and the chlorine-containing compound, and examples thereof include an ether, a sulfide, an amine, a carbonate ester, a carbamate ester, urea, a chlorocarbonate ester, a chlorocarbonate thioester, a carbamoyl chloride, an isocyanate, a sulfonate, a silyl ether, a phosphonate ester, an ester, a thioester, an amide, an acid anhydride, an imide, and a silyl ester.

Specifically, for example, compounds represented by the formulae (9) to (34) are obtained as the products from the reaction substrates represented by the above formulae (a1) to (a3) and the chlorine-containing compounds represented by the formulae (1) to (8) or synthetic equivalents thereof.

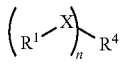 (9)

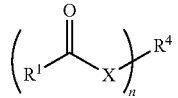 (10)

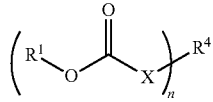 (11)

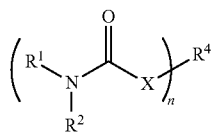 (12)

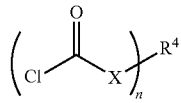 (13)

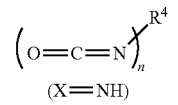 (14)

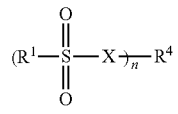 (15)

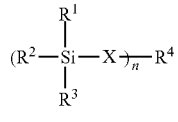 (16)

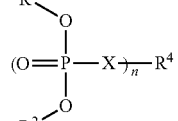 (17)

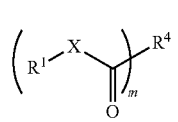 (18)

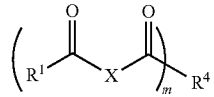 (19)

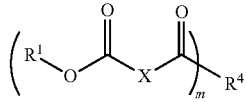 (20)

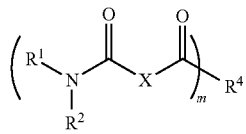 (21)

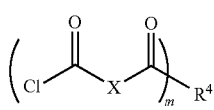 (22)

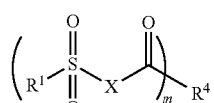 (23)

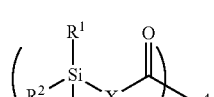 (24)

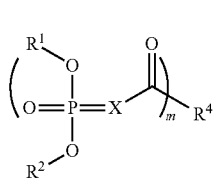 (25)

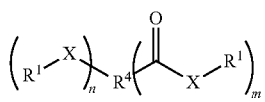 (26)

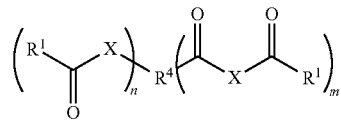 (27)

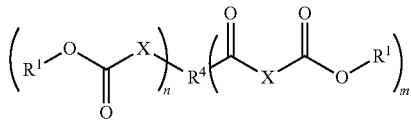 (28)

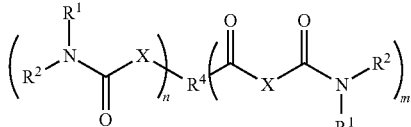 (29)

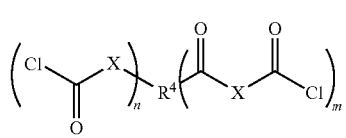 (30)

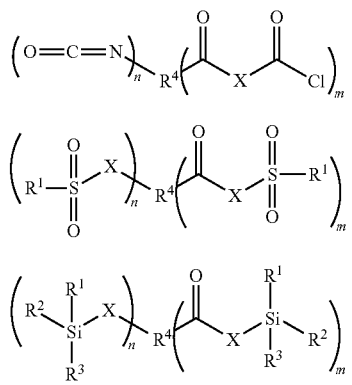
(31)
(32)
(33)
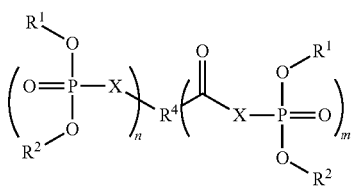
(34)
Here, in the formulae, $R^1$ to $R^4$, X, n, and m are the same as above.
Incidentally, the reaction substrate and the chlorine-containing compound can be appropriately combined, and particularly, the following combinations are preferred, and the products obtained at that time are as follows.
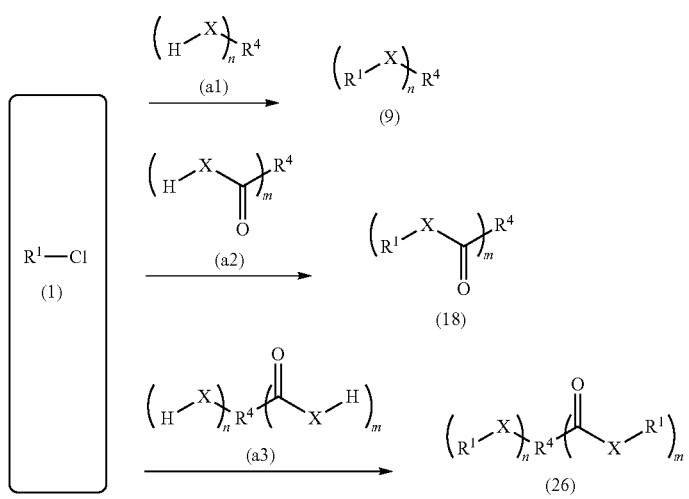
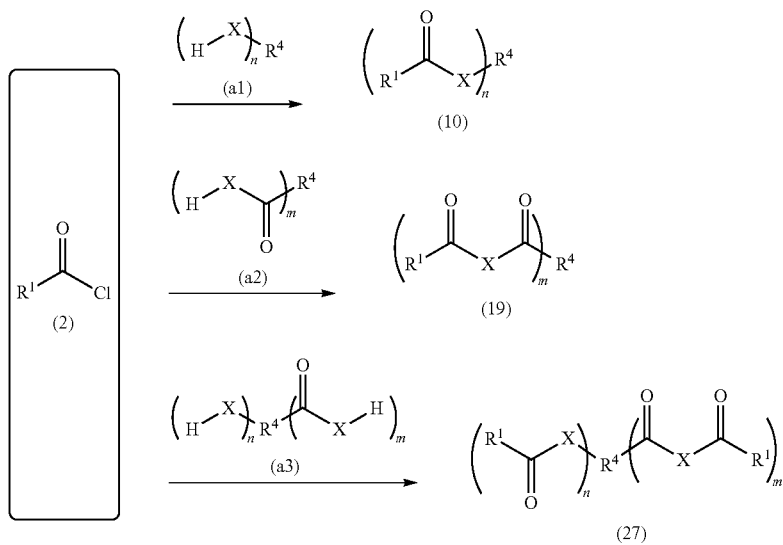

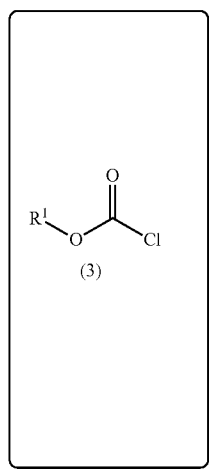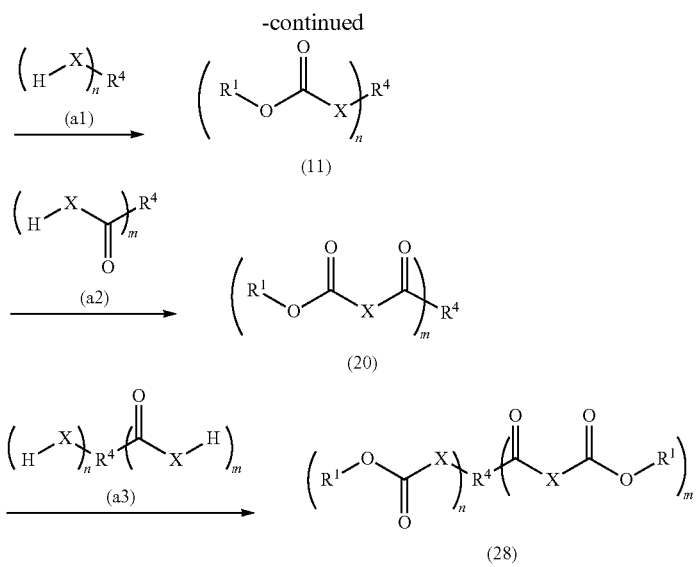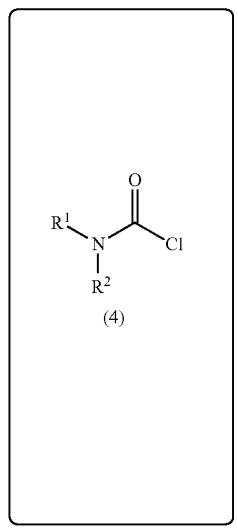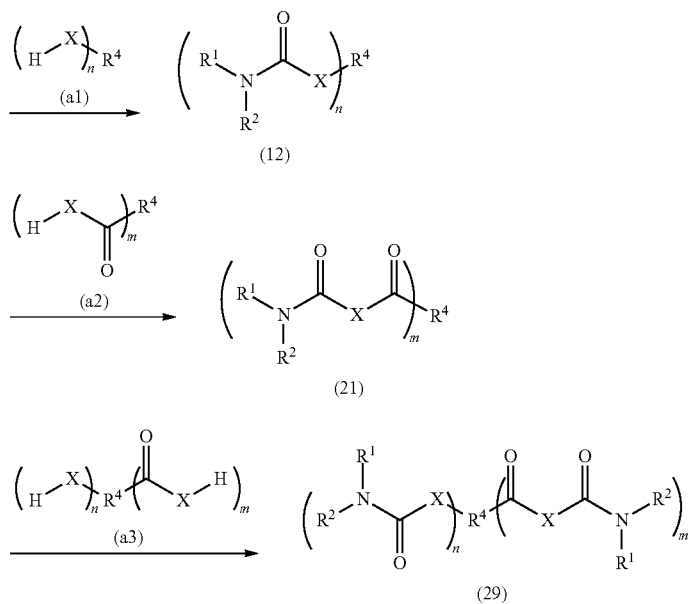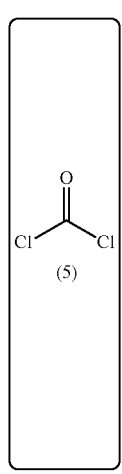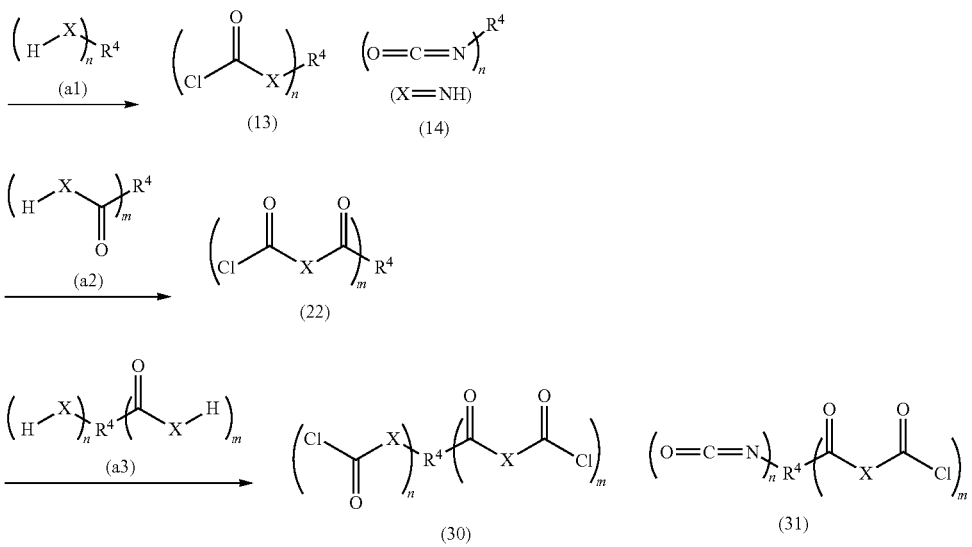

-continued
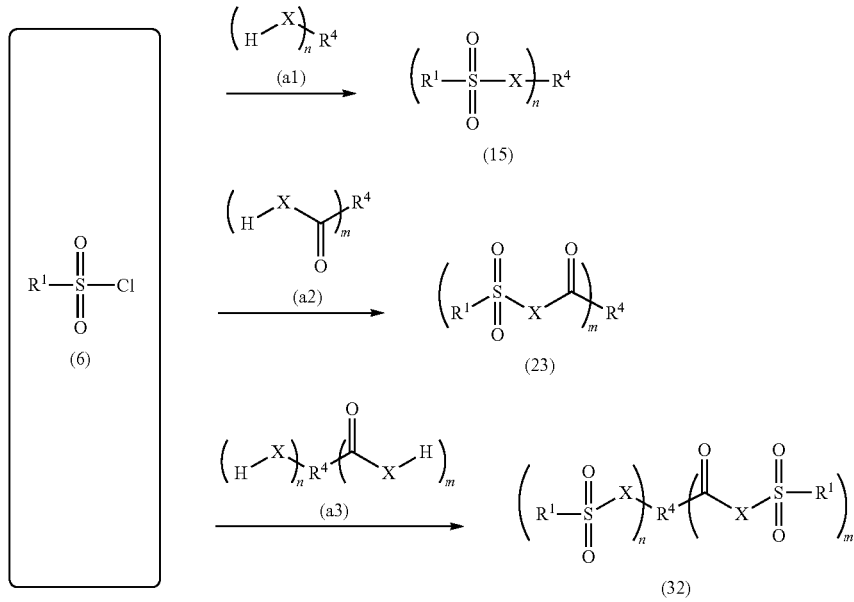
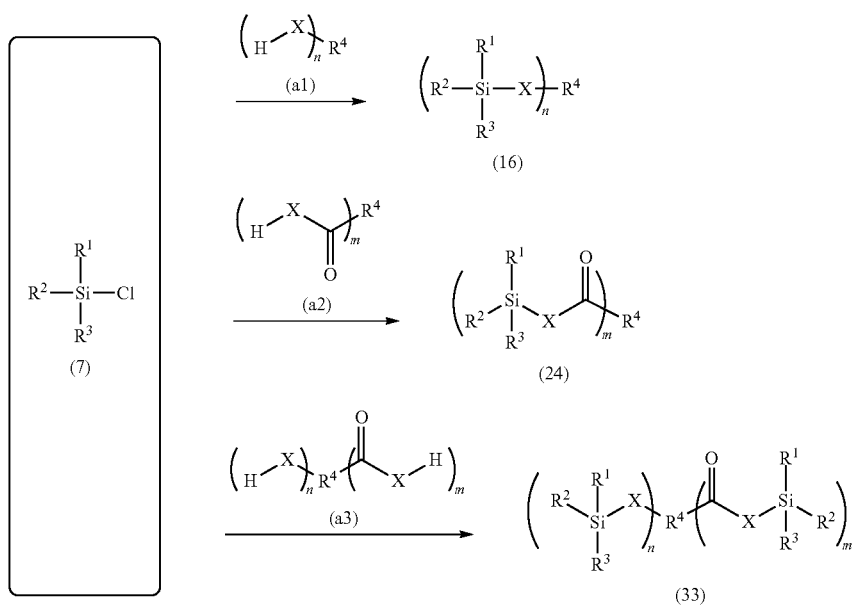

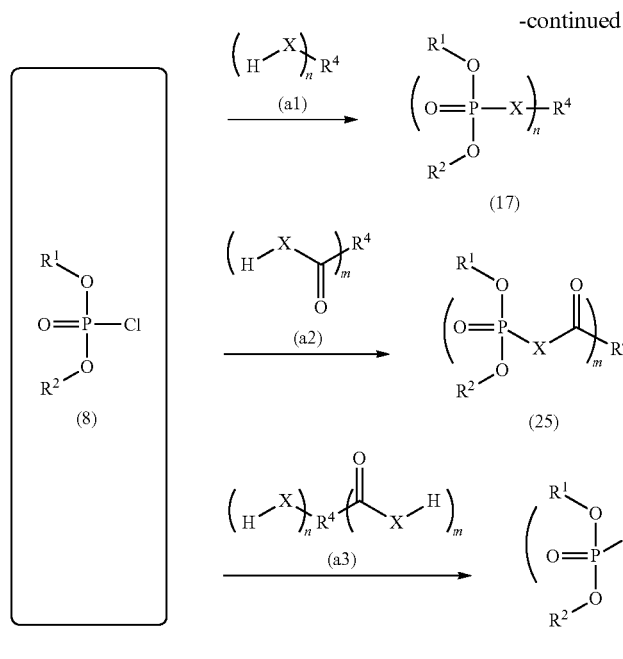
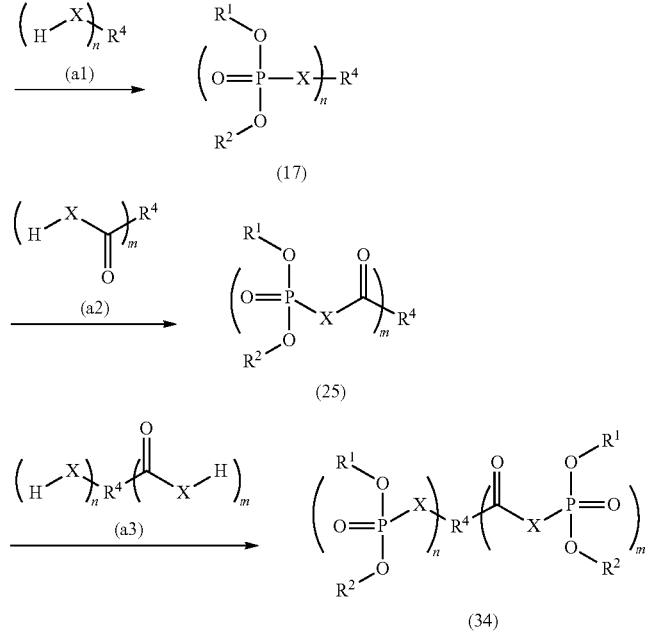

For example, (2R,3R)-3-(2,4-difluorophenyl)-3,4-epoxy-2-butylsulfonate (one of the compounds of the formula (15)) is obtained as the product by reacting (2R,3R)-3-(2,4-difluorophenyl)-3,4-epoxy-2-butyl alcohol (one of the compounds of the formula (a1)) which is a preferred reaction substrate with a sulfonyl chloride compound (one of the compounds of the formula (6)). Particularly, (2R,3R)-3-(2,4-difluorophenyl)-3,4-epoxy-2-butylmethanesulfonate is preferably obtained as the product by reacting (2R,3R)-3-(2,4-difluorophenyl)-3,4-epoxy-2-butyl alcohol with methanesulfonyl chloride.

Further, benzyl benzoate (one of the compounds of the formula (10)) is obtained as the product by reacting benzyl alcohol (one of the compounds of the formula (a1)) which is a reaction substrate with benzoyl chloride (one of the compounds of the formula (2)).

When (R)-1-phenylethylamine (one of the compounds of the formula (a1)) as a reaction substrate is reacted with benzoyl chloride (one of the compounds of the formula (2)), (R)—N-benzoyl-α-phenylethylamine (one of the compounds of the formula (10)) is obtained as the product.

When (S)-1-phenyl-1,2,3,4-tetrahydroisoquinoline (one of the compounds of the formula (a1)) as a reaction substrate is reacted with phosgene (5) or a synthetic equivalent thereof, (S)-1-phenyl-1,2,3,4-tetrahydroisoquinolinecarbonyl chloride (one of the compounds of the formula (13)) is obtained as the product.

The products obtained from the reaction substrates represented by the formulae (a1) to (a3) are preferably benzyl benzoate, (R)—N-benzoyl-α-phenylethylamine, (S)-1-phenyl-1,2,3,4-tetrahydroisoquinolinecarbonyl chloride, and (2R,3R)-3-(2,4-difluorophenyl)-3,4-epoxy-2-butylmethanesulfonate, and particularly preferably (2R,3R)-3-(2,4-difluorophenyl)-3,4-epoxy-2-butylmethanesulfonate.

When the basic compound is phosgene (5) or a synthetic equivalent thereof, two chlorine reactive groups may be reacted with and bonded to one phosgene. For example, when two XH groups of the each reaction substrates (a4) to (a6) are reacted with one phosgene (5), compounds represented by the following formulae (35) to (37) are obtained as the products.

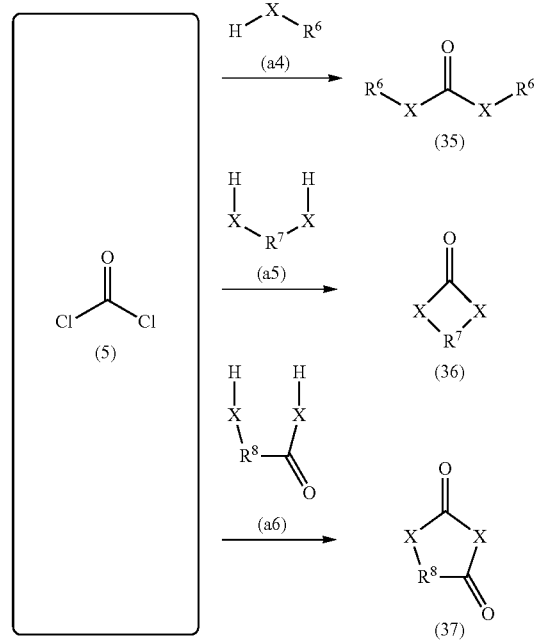

(In the formulae (35) to (37), $R^6$ to $R^8$, and X are the same as above.)

For example, N-[1-(S)-ethoxycarbonyl-3-phenylpropyl]-L-alanyl-N-carboxylic acid anhydride (one of the compounds of the formula (37)), benzyl 4-({[(2S,5R)-6-(benzyloxy)-7-oxo-1,6-diazabicyclo[3.2.1.]oct-2-yl] carbamoyl}amino)piperidine-1-carboxylate (one of the compounds of the formula (36)), tert-butyl 4-({[(2S,5R)-6-(benzyloxy)-7-oxo-1,6-diazabicyclo[3.2.1.]oct-2-yl]

carbamoyl}amino)piperidine-1-carboxylate (one of the compounds of the formula (36)), benzyl (4R,6S)-3-(benzyloxy)-2-oxo-1,3-diazabicyclo[2,2,1]heptane-6-carboxylate (one of the compounds of the formula (36)), methyl (4R,6S)-3-(benzyloxy)-2-oxo-1,3-diazabicyclo[2,2,1]heptane-6-carboxylate (one of the compounds of the formula (36)), or (4R,6S)-3-(benzyloxy)-2-oxo-1,3-diazabicyclo[2,2,1]heptane-6-carboxamide (one of the compounds of the formula (36)) is obtained as the product by reacting N-[1-(S)-ethoxycarbonyl-3-phenylpropyl]-L-alanine (one of the compounds of the formula (a6)), benzyl 4-[({(2S,5R)-5-[(benzyloxy)amino]piperidin-2-yl}carbonyl)amino]piperidine-1-carboxylate (one of the compounds of the formula (a5)), tert-butyl 4-[({(2S,5R)-5-[(benzyloxy)amino]piperidin-2-yl}carbonyl)amino]piperidine-1-carboxylate (one of the compounds of the formula (a5)), benzyl (2S,5R)-5-benzyloxyamino-piperidine-2-carboxylate (one of the compounds of the formula (a5)), methyl (2S,5R)-5-benzyloxyamino-piperidine-2-carboxylate (one of the compounds of the formula (a5)), or (2S,5R)-5-benzyloxyamino-piperidine-2-carboxamide (one of the compounds of the formula (a5)) which is a preferred reaction substrate with phosgene or triphosgene.

In the present invention, when the reaction is carried out in a flow reactor, a trialkyl amine having 9 to 40 carbon atoms is used. When the trialkyl amine having 9 to 40 carbon atoms is used, the risk of precipitating a chloride thereof as a solid is greatly reduced, and thus the fear of blocking the reaction in the flow reactor is decreased. From the viewpoint of reducing precipitation of the solid, the trialkyl amine is preferably a noncyclic trialkyl amine.

The number of carbon atoms of the trialkyl amine may be 10 or more or 12 or more, and may be 40 or less, or 30 or less, or 24 or less. Examples of the trialkyl amine include tripropylamine, tributylamine, tripentylamine, trihexylamine, triheptylamine, trioctylamine, tridodecylamine, dodecyldimethylamine, hexyldibutylamine, and diisopropylbutylamine. These trialkyl amines may be used alone or in combination two or more kinds. When mixing two or more kinds of the trialkyl amine, there is no restriction on the mixing ratio thereof. From the viewpoint of availability, tripropylamine, tributylamine, trihexylamine, and trioctylamine are preferable, and tributylamine is more preferable.

The using amount of the trialkyl amine is, for example, 0.1 mol or more, preferably 0.5 mol or more, more preferably 0.8 mol or more, and is, for example, 15 mol or less, preferably 8 mol or less, and more preferably 4 mol or less, relative to 1 mol of the chlorine reactive group contained in the reaction substrate.

The using amount of the trialkyl amine is, for example, 0.2 mol or more, preferably 0.5 mol or more, more preferably 0.8 mol or more, and is, for example, 4 mol or less, preferably 3 mol or less, and more preferably 2 mol or less, relative to 1 mol of chlorine atoms in the chlorine-containing compound.

The aforementioned reaction is carried out in an organic solvent. In the present invention, the specific trialkyl amine is used, and thus, the fear of clogging the flow reactor by precipitation of a chloride thereof in the reactor can be reduced. Therefore, the range of choice of the organic solvent can be increased, and various organic solvents can be used. Examples of the organic solvent which can be used in the present invention include an aliphatic hydrocarbon solvent such as n-hexane, cyclohexane, and methylcyclohexane; an aromatic hydrocarbon solvent such as benzene, toluene, and xylene; an ether solvent such as diethyl ether, diisopropyl ether, tetrahydrofuran, 2-methyltetrahydrofuran, 4-methyltetrahydropyran, methyl tert-butyl ether, 1,4-dioxane, and cyclopentyl methyl ether; a halogen-containing solvent such as dichloromethane, chloroform, 1,1,1-trichloroethane, and chlorobenzene; an ester solvent such as ethyl acetate, propyl acetate, and butyl acetate; a ketone solvent such as acetone, methyl ethyl ketone, and methyl isobutyl ketone; a nitrile solvent such as acetonitrile, propionitrile, and butyronitrile; and an amide solvent such as N,N-dimethylformamide, N,N-dimethylacetamide, and N-methylpyrrolidone. These solvents may be used alone or in combination two or more kinds, and there is no restriction on the mixing ratio thereof.

In the present invention, a non-halogen solvent, particularly, an aliphatic hydrocarbon solvent, an aromatic hydrocarbon solvent, an ether solvent, an ester solvent, a ketone solvent, a nitrile solvent, an amide solvent, and the like are preferred. When using a halogen-containing solvent, precipitation of even diisopropylethylamine hydrochloride can be suppressed, however, when using a non-halogen solvent, precipitation may occur. With the use of the amine of the present invention, even when using a non-halogen solvent, precipitation of a hydrochloride can be suppressed.

From a similar point of view, in the present invention, a solvent other than a halogen-containing solvent, an aromatic hydrocarbon solvent, a ketone solvent, a nitrile solvent, and an amide solvent, for example, an aliphatic hydrocarbon solvent, an ether solvent, an ester solvent, and the like are preferred, and particularly, an ether solvent and an ester solvent are preferred.

Further, in the present invention, whichever solvent is selected, clogging can be prevented. Therefore, a preferred solvent can be selected freely from the viewpoint other than prevention of occlusion, for example, from the viewpoint of reactivity, post treatment, or the like. From such a viewpoint, the solvent is preferably an aromatic hydrocarbon solvent such as benzene, toluene, and xylene; an ether solvent such as diethyl ether, diisopropyl ether, tetrahydrofuran, 2-methyltetrahydrofuran, 4-methyltetrahydropyran, methyl t-butyl ether, 1,4-dioxane, and cyclopentyl methyl ether; and a nitrile solvent such as acetonitrile, propionitrile, and butyronitrile, and more preferably toluene, tetrahydrofuran, and acetonitrile.

In the present invention, water may coexist as needed. The coexistence of water can more highly prevent an amine hydrochloride from precipitating. In the present invention, however, precipitation of an amine hydrochloride can be prevented even without coexistence of water. That is, the present invention also has an advantage in that even when water is not favorable, the reaction can be carried out without worrying about clogging due to precipitation of an amine hydrochloride. When water does not coexist, the concentration of water in the total solvent (particularly, the concentration during the reaction) is, for example, 10 wt % or less, preferably 5 wt % or less, and more preferably 1 wt % or less.

The using amount of the solvent can be determined within a range that the reaction substrate and the product can be dissolved during the reaction, that is, during the coexistence of the reaction substrate, the chlorine-containing compound, and the trialkyl amine. The amount of the solvent during the coexistence of the reaction substrate, the chlorine-containing compound, and the trialkyl amine is, for example, 0.1 parts by weight or more, preferably 0.5 parts by weight or more, more preferably 1 part by weight or more, and is, for example, 100 parts by weight or less, preferably 50 parts by weight or less, more preferably 30 parts by weight or less, and particularly preferably 10 parts by weight or less, relative to 1 part by weight of the reaction substrate.

The amount of the trialkyl amine during the reaction (that is, during the coexistence of the reaction substrate, the chlorine-containing compound, and the trialkyl amine) is, for example, 3 parts by weight or more, preferably 10 parts by weight or more, more preferably 15 parts by weight or more, particularly preferably 20 parts by weight or more, and most preferably 25 parts by weight or more, and is, for example, 60 parts by weight or less, preferably 50 parts by weight or less, and more preferably 45 parts by weight or less, relative to 100 parts by weight of the solvent.

In the present invention, the above-mentioned reaction is carried out in a flow reactor. The flow reactor is an apparatus having two or more raw material feeding ports, a mixing unit to mix the fed raw materials, and a reactor unit in which a mixed solution flows. The reactor unit can have different shape such as a micro flow tube having a coil structure, a plate structure in which a micro flow channel is engraved on a plate, or a laminated structure in which these plates are stacked. The reaction progresses while the mixed solution flows in the reactor unit. The raw materials are fed in the form of a liquid (including a solution), and the liquid is usually transferred using a pump such as a diaphragm pump, a syringe pump, a plunger pump or the like. The raw material feeding ports, the mixing unit, and the reactor unit are liquid-tightly connected.

The reaction substrate, the chlorine-containing compound, and the trialkyl amine are all fed as an organic solvent solution from the raw material feeding ports to the mixing unit. The reaction substrate, the chlorine-containing compound, and the trialkyl amine are all separately dissolved and may be fed from different feeding ports. Further, an organic solvent solution containing part of the reaction substrate, the chlorine-containing compound, and the trialkyl amine, particularly, solution containing the reaction substrate and the trialkyl amine is prepared in advance, and this partially mixed solution and an organic solvent solution of the rest of the raw material (particularly, the chlorine-containing compound) may be fed from different feeding ports. For the raw material liquids obtained by separate dissolution, the same organic solvent may be used, and mutually different organic solvents may be used.

A known mixer can be used for the mixing unit. For example, a T-shape mixer (including a T-shape tube) and a Y-shape mixer (including a Y-shape tube) can be used as a mixer having two inflow channels and one outflow line. A mixing unit having three or more inflow channels can also be used as the mixing unit (mixer). The mixing unit (mixer) may be a static-type mixer, or a helix-type mixer.

The number of the mixing units (mixers) is suitably determined depending on the number of inflow channels and the number of raw material feeding ports of one mixing unit. For example, in the case where three raw material feeding ports are present, and a reaction substrate solution, a chlorine-containing compound solution, and a trialkyl amine solution are separately fed, a liquid containing all the components can be mixed in one mixing unit by using a mixing unit having three inflow channels. Further, when a reaction substrate solution, a chlorine-containing compound solution, and a trialkyl amine solution are separately fed, a mixing unit having two inflow channels can also be used. In this case, for example, two mixing units may be prepared, and a reaction substrate solution and a chlorine-containing compound solution are mixed in a first mixing unit, and then an outflow liquid from the first mixing unit and a trialkyl amine solution may be mixed in a next mixing unit (a first method), alternatively, a reaction substrate solution and a trialkyl amine solution are mixed in a first mixing unit, and then an outflow liquid from the first mixing unit and a chlorine-containing compound solution may be mixed in a next mixing unit (a second method). The second method is superior from the viewpoint that the chlorine-containing compound can be prevented from reacting before mixing all the components. Further, when one mixer having two raw material feeding ports and one inflow channel is used, a mixed liquid of the reaction substrate and the trialkyl amine and a chlorine-containing compound solution may be separately introduced from the raw material feeding ports, and mixed with each other.

The mixed solution prepared in the mixing unit is fed to the reactor unit, and the reaction proceeds while the mixed solution flows in the reactor unit. The shape of the reactor unit is not particularly limited, and may be a micro flow tube having a coil structure, a plate structure in which a micro flow channel is engraved on a plate, or a laminated structure in which these plates are stacked. The reaction time is controlled by the length of the reactor unit (retention line) and the flow rate. The length of the reactor unit is, for example, 1 cm or more and 500 m or less, preferably 10 cm or more and 300 m or less, and more preferably 1 m or more and 100 m or less. The cross-sectional area of the flow channel of the mixing unit and the reactor unit is, for example, 10 $\mu m^2$ or more and 300 $cm^2$ or less, preferably 1 $mm^2$ or more and 70 $cm^2$ or less, and more preferably 10 $mm^2$ or more and 30 $cm^2$ or less. The linear velocity is, for example, 0.005 m/min or more and 180 m/min or less, preferably 0.05 m/min or more and 120 m/min or less, and more preferably 0.5 m/min or more and 60 m/min or less. The reaction time (retention time) is, for example, 30 minutes or less, preferably 20 minutes or less, more preferably 15 minutes or less, and is, for example, 5 minutes or more, preferably 3 minutes or more, and more preferably 1 minute or more.

The reaction temperature can be set within the range of from the freezing point to the boiling point of the solvent. The reaction temperature is, for example, 100° C. or lower, preferably 80° C. or lower, more preferably 60° C. or lower, and is, for example, −50° C. or higher, preferably −30° C. or higher, and more preferably −10° C. or higher. The temperature of the mixture and the temperature on the upstream side of the mixture may also be appropriately set, and, for example, may be the same as the reaction temperature. These temperatures may also be lower than the reaction temperature in order to improve the heat removal efficiency.

The materials of the mixing unit and the reactor unit are not particularly limited and may be appropriately selected depending on needs for solvent resistance, pressure resistance, heat resistance, or the like. For example, a metal such as stainless steel, Hastelloy, titanium, copper, nickel and aluminum; a glass; a ceramics; and a resin such as PEEK resin, silicone resin, and fluororesin can be used.

As the flow reactor, a known device such as a microreactor, a cyclone-shaped reactor, and a laminated microfluidic chip can be appropriately utilized.

The reaction solution flowing out from the reactor unit is appropriately post-treated as necessary. For example, an organic solvent such as ethyl acetate or toluene may be optionally added to extract an intended product, after quenching the reaction solution with water or an aqueous solution such as water; an acidic aqueous solution containing hydrochloric acid, sulfuric acid, phosphoric acid, acetic acid, citric acid, or the like; and an alkaline aqueous solution containing sodium hydroxide, potassium carbonate, or sodium hydrogen carbonate. The using amount of water, the acidic aqueous solution, or the alkaline aqueous solution to be used for quenching is not particularly limited, however, the lower limit thereof is generally 0.1 times by weight, preferably 0.5 times by weight, and more preferably 1 time by weight, and the upper limit thereof is generally 100 times by weight, preferably 50 times by weight, and more preferably 20 times by weight, with respect to the reaction substrate. An organic solvent such as ethyl acetate or toluene may be optionally added, and quenching may be carried out in a two-layer system of water-organic solvent. In addition, the extract can also be washed with acidic water, inorganic salt water or water as necessary. The reaction solvent and the extraction solvent are distilled away from the resultant extract by an operation such as heating under reduced pressure or the like, whereby an intended product is obtained.

The intended product thus obtained has sufficient purity to be used in a subsequent step. The purity may be further increased by using a commonly used purification technique such as crystallization, fractional distillation, column chromatography, or the like.

The present application claims the benefit of priority based on Japanese Patent Application No. 2016-143646 filed on Jul. 21, 2016. The entire contents of the specification of Japanese Patent Application No. 2016-143646 filed on Jul. 21, 2016 are incorporated herein by reference.

EXAMPLES

Hereinafter, the present invention will be more specifically described with reference to Examples, however, as a matter of course, the invention is not limited by the following Examples, and can also be carried out by appropriately adding modifications within a scope applicable to the gist described above and below, and all such modifications are encompassed within the technical scope of the present invention.

Reference Example 1

Each of 1 g of various amines shown in the following Table 1 was added to 10 mL of each solvent shown in the following Table 1 to prepare a 10% concentration (weight/volume) solution. An n-propanol solution of hydrochloric acid (hydrochloric acid concentration: 34% by weight) was added to this solution until reaching 1.1 equivalents (=molar amount of hydrogen chloride/molar amount of amine), and the mixture was stirred for 1 hour at room temperature. After stirring, whether solids were precipitated or not was visually confirmed. In the table, "Good" means that no solid was precipitated, and "Poor" means that solid was precipitated.

(1) Production of (2R,3R)-3-(2,4-difluorophenyl)-3,4-epoxy-2-butylmethanesulfonate

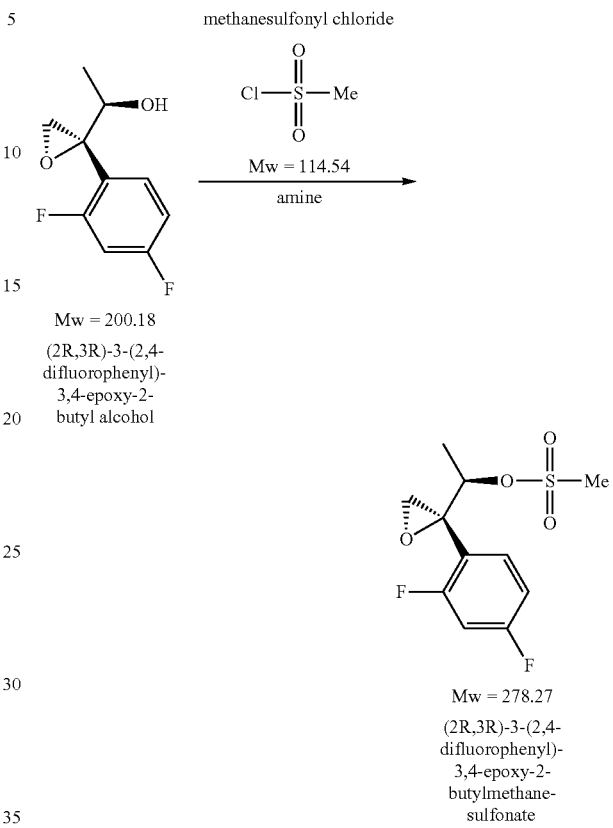

Evaluation Method 1

In the following Examples 1 to 4 and Comparative Examples 1 and 2, (2R,3R)-3-(2,4-difluorophenyl)-3,4-epoxy-2-butylmethanesulfonate was produced from (2R,3R)-3-(2,4-difluorophenyl)-3,4-epoxy-2-butyl alcohol and methanesulfonyl chloride. The product was quantified by the HPLC method to calculate the yield. HPLC conditions were as follows.

Column: SHISEIDO CAPCELLPAC C18 TYPE MG (250×4.6 mm)
Mobile phase A: 0.1% phosphoric acid aqueous solution
Mobile phase B: acetonitrile
Flow rate: 1.0 ml/min
Detection wavelength: UV 210 nm

TABLE 1

| | | Number of carbon atoms | Solvent[*2] | | | | | | | |
|---|---|---|---|---|---|---|---|---|---|---|
| | | | THF | MTBE | IPRA | ACE | DMF | AN | Tol | DCM |
| Amine[*1] | TEA | 6 | Poor | Poor | Poor | Poor | Poor | Poor | Poor | Good |
| | DIPEA | 8 | Poor | Poor | Poor | Good | Good | Good | Good | Good |
| | TPA | 9 | Good | Good | Good | Good | Good | Good | Good | Good |
| | TBA | 12 | Good | Good | Good | Good | Good | Good | Good | Good |
| | TOA | 24 | Good | Good | Good | Good | Good | Good | Good | Good |
| | DBU | Cyclic amine | Poor | Poor | Poor | Good | Good | Good | Good | Good |
| | LTD | Aromatic amine | Poor | Poor | Poor | Poor | Poor | Poor | Poor | Good |

[*1]Amine used Triethylamine (TEA), diisopropylethylamine (DIPEA), tripropylamine (TPA), tributylamine (TBA), trioctylamine (TOA), 1,8-diazabicyclo[5,4,0]undec-7-ene (DBU), and 2,6-lutidine (LTD)
[*2]Solvent used Tetrahydrofuran (THF), methyl tert-butyl ether (MTBE), isopropyl acetate (IPRA), acetone (ACE), N,N-dimethylformamide (DMF), acetonitrile (AN), toluene (Tol), and dichloromethane (DCM)

Column temperature: 30° C.
Retention time: (2R,3R)-3-(2,4-difluorophenyl)-3,4-epoxy-2-butylmethanesulfonate: 28.1 minutes
Gradient conditions

| Time (min) | Mobile phase A (%) | Mobile phase B (%) |
|---|---|---|
| 0 | 70 | 30 |
| 15 | 70 | 30 |
| 25 | 40 | 60 |
| 45 | 40 | 60 |
| 50 | 10 | 90 |
| 60 | 10 | 90 |

Example 1

To 3.00 g of (2R,3R)-3-(2,4-difluorophenyl)-3,4-epoxy-2-butyl alcohol, 5.54 g of toluene and 4.44 g of tributylamine were added to prepare a homogeneous solution, and the resulting solution was referred to as solution A. To 2.57 g of methanesulfonyl chloride, 10.68 g of toluene was added to prepare a homogeneous solution, and the resulting solution was referred to as solution B. A T-shape mixer (inner diameter: 2 mm, material: polytetrafluoroethylene (PTFE)) and a retention line (inner diameter of tube: 2 mm, material: polytetrafluoroethylene (PTFE)) were placed in a constant-temperature bath at 50° C. Then, the solution A and the solution B were each transferred using a diaphragm pump (manufactured by KNF Japan Co. Ltd.) at a rate of 2 ml/min and mixed by the T-shape mixer, and the resulting mixture was allowed to flow in the retention line for 12 minutes to perform a reaction (amine/solvent=27.5/100 (weight ratio)). The reaction solution was continuously quenched while stirring with 6.00 g of water in a flask. After separation, 47.08 g of an organic layer containing 4.08 g of (2R,3R)-3-(2,4-difluorophenyl)-3,4-epoxy-2-butylmethanesulfonate was obtained (yield: 98%). No crystals precipitated during the reaction, and the reaction solution was a clear solution.

Example 2

To 3.00 g of (2R,3R)-3-(2,4-difluorophenyl)-3,4-epoxy-2-butyl alcohol, 5.54 g of toluene and 4.44 g of tributylamine were added to prepare a homogeneous solution, and the resulting solution was referred to as solution A. To 2.57 g of methanesulfonyl chloride, 10.68 g of toluene was added to prepare a homogeneous solution, and the resulting solution was referred to as solution B. A T-shape mixer (inner diameter: 2 mm, material: polytetrafluoroethylene (PTFE)) and a retention line (inner diameter of tube: 2 mm, material: polytetrafluoroethylene (PTFE)) were placed in a constant-temperature bath at 0° C. Then, the solution A and the solution B were each transferred using a diaphragm pump (manufactured by KNF Japan Co. Ltd.) at a rate of 2 ml/min and mixed by the T-shape mixer, and the resulting mixture was allowed to flow in the retention line for 3 minutes to perform a reaction (amine/solvent=27.5/100 (weight ratio)). The reaction solution was continuously quenched while stirring with 6.00 g of water in a flask. After separation, 41.34 g of an organic layer containing 4.13 g of (2R,3R)-3-(2,4-difluorophenyl)-3,4-epoxy-2-butylmethanesulfonate was obtained (yield: 99%). No crystals precipitated during the reaction, and the reaction solution was a clear solution.

Example 3

To 3.00 g of (2R,3R)-3-(2,4-difluorophenyl)-3,4-epoxy-2-butyl alcohol, 5.54 g of toluene and 3.44 g of tripropylamine were added to prepare a homogeneous solution, and the resulting solution was referred to as solution A. To 2.57 g of methanesulfonyl chloride, 9.68 g of toluene was added to prepare a homogeneous solution, and the resulting solution was referred to as solution B. A T-shape mixer (inner diameter: 2 mm, material: polytetrafluoroethylene (PTFE)) and a retention line (inner diameter of tube: 2 mm, material: polytetrafluoroethylene (PTFE)) were placed in a constant-temperature bath at 0° C. Then, the solution A and the solution B were each transferred using a diaphragm pump (manufactured by KNF Japan Co. Ltd.) at a rate of 2 ml/min and mixed by the T-shape mixer, and the resulting mixture was allowed to flow in the retention line for 12 minutes to perform a reaction (amine/solvent=22.7/100 (weight ratio)). The reaction solution was continuously quenched while stirring with 6.00 g of water in a flask. After separation, 46.90 g of an organic layer containing 4.17 g of (2R,3R)-3-(2,4-difluorophenyl)-3,4-epoxy-2-butylmethanesulfonate was obtained (yield: 100%). No crystals precipitated during the reaction, and the reaction solution was a clear solution.

Example 4

To 3.00 g of (2R,3R)-3-(2,4-difluorophenyl)-3,4-epoxy-2-butyl alcohol, 5.54 g of toluene and 8.48 g of trioctylamine were added to prepare a homogeneous solution, and the resulting solution was referred to as solution A. To 2.57 g of methanesulfonyl chloride, 14.68 g of toluene was added to prepare a homogeneous solution, and the resulting solution was referred to as solution B. A T-shape mixer (inner diameter: 2 mm, material: polytetrafluoroethylene (PTFE)) and a retention line (inner diameter of tube: 2 mm, material: polytetrafluoroethylene (PTFE)) were placed in a constant-temperature bath at 0° C. Then, the solution A and the solution B were each transferred using a diaphragm pump (manufactured by KNF Japan Co. Ltd.) at a rate of 2 ml/min and mixed by the T-shape mixer, and the resulting mixture was allowed to flow in the retention line for 12 minutes to perform a reaction (amine/solvent=42.1/100 (weight ratio)). The reaction solution was continuously quenched while stirring with 6.00 g of water in a flask. After separation, 62.38 g of an organic layer containing 3.96 g of (2R,3R)-3-(2,4-difluorophenyl)-3,4-epoxy-2-butylmethanesulfonate was obtained (yield: 95%). No crystals precipitated during the reaction, and the reaction solution was a clear solution.

Comparative Example 1 (Batch Method)

In a flask, 1.00 g of (2R,3R)-3-(2,4-difluorophenyl)-3,4-epoxy-2-butyl alcohol, 11.00 g of toluene, 10.20 g of THF, and 0.66 g of triethylamine were placed, and the inner temperature was adjusted to 0° C. while stirring. Thereafter, 0.69 g of methanesulfonyl chloride was slowly added thereto at a rate of keeping the same inner temperature, and after completion of the addition, the resulting mixture was stirred at 0° C. for 1 hour (amine/solvent=3.1/100 (weight ratio)). Subsequently, the reaction solution was quenched by adding 2 g of water thereto. After separation, 22.86 g of an organic layer containing 1.38 g of (2R,3R)-3-(2,4-difluorophenyl)-3,4-epoxy-2-butylmethanesulfonate was obtained (yield: 99%). Although the amine concentration was lower than in the Reference Example, a crystal was precipitated during the reaction, and the reaction solution was a slurry.

Comparative Example 2 (Batch Method)

In a flask, 1.00 g of (2R,3R)-3-(2,4-difluorophenyl)-3,4-epoxy-2-butyl alcohol, 9.42 g of toluene, and 0.66 g of triethylamine were placed, and the inner temperature was adjusted to 0° C. while stirring. Thereafter, 0.69 g of methanesulfonyl chloride was slowly added thereto at a rate of keeping the same inner temperature, and after completion of the addition, the resulting mixture was stirred at 0° C. for 1 hour (amine/solvent=7.0/100 (weight ratio)). Subsequently, the reaction solution was quenched by adding 2 g of water thereto. After separation, 10.84 g of an organic layer containing 1.31 g of (2R,3R)-3-(2,4-difluorophenyl)-3,4-epoxy-2-butylmethanesulfonate was obtained (yield: 94%). Although the amine concentration was lower than in the Reference Example, a crystal was precipitated during the reaction, and the reaction solution was a slurry.

(2) Production of Benzyl Benzoate

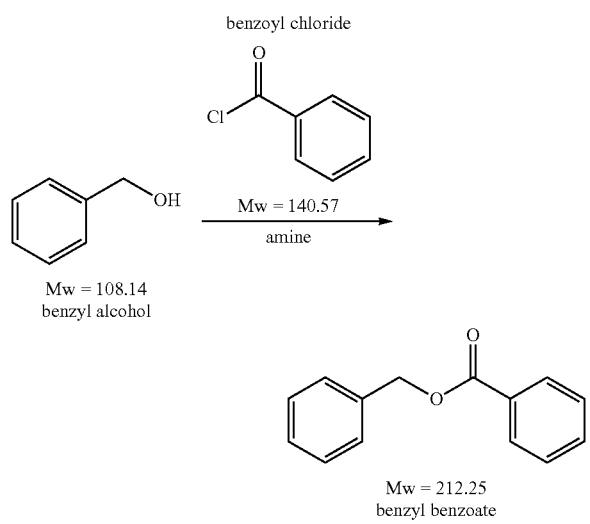

Evaluation Method 2

In the following Examples 5 to 6 and Comparative Example 3, benzyl benzoate was produced from benzyl alcohol and benzoyl chloride. The product was quantified by the HPLC method to calculate the yield. HPLC conditions were as follows.

Column: Zorbax Eclipse Plus C18 (50×4.6 mm, 1.8 μm)
Mobile phase A: 0.1% phosphoric acid aqueous solution
Mobile phase B: acetonitrile
Flow rate: 1.0 ml/min
Detection wavelength: UV 254 nm
Column temperature: 40° C.
Retention time: benzyl benzoate: 13 minutes
Gradient conditions

| Time (min) | Mobile phase A (%) | Mobile phase B (%) |
|---|---|---|
| 0 | 90 | 10 |
| 10 | 45 | 55 |
| 18 | 45 | 55 |
| 23 | 5 | 95 |

Example 5

To 3.00 g of benzyl alcohol, 5.00 g of toluene and 6.68 g of tributylamine were added to prepare a homogeneous solution, and the resulting solution was referred to as solution A. To 4.68 g of benzoyl chloride, 11.79 g of toluene was added to prepare a homogeneous solution, and the resulting solution was referred to as solution B. A T-shape mixer (inner diameter: 2 mm, material: polytetrafluoroethylene (PTFE)) and a retention line (inner diameter of tube: 2 mm, material: polytetrafluoroethylene (PTFE)) were placed in a constant-temperature bath at 20° C. Then, the solution A and the solution B were each transferred using a diaphragm pump (manufactured by KNF Japan Co. Ltd.) at a rate of 2 ml/min and mixed by the T-shape mixer, and the resulting mixture was allowed to flow in the retention line for 2 minutes to perform a reaction (amine/solvent=39.8/100 (weight ratio)). The reaction solution was continuously quenched while stirring with 10.00 g of water in a flask. After separation, 36.58 g of an organic layer containing 5.71 g of benzyl benzoate was obtained (yield: 97%). No crystals precipitated during the reaction, and the reaction solution was a clear solution.

Example 6

To 3.00 g of benzyl alcohol, 5.00 g of a mixed solution of acetonitrile/toluene (weight ratio: 10/1) and 5.96 g of tripropylamine were added to prepare a homogeneous solution, and the resulting solution was referred to as solution A. To 5.46 g of benzoyl chloride, 9.94 g of a mixed solution of acetonitrile/toluene (weight ratio: 10/1) was added to prepare a homogeneous solution, and the resulting solution was referred to as solution B. A T-shape mixer (inner diameter: 2 mm, material: polytetrafluoroethylene (PTFE)) and a retention line (inner diameter of tube: 2 mm, material: polytetrafluoroethylene (PTFE)) were placed in a constant-temperature bath at 20° C. Then, the solution A and the solution B were each transferred using a diaphragm pump (manufactured by KNF Japan Co. Ltd.) at a rate of 2 ml/min and mixed by the T-shape mixer, and the resulting mixture was allowed to flow in the retention line for 8 minutes to perform a reaction (amine/solvent=39.9/100 (weight ratio)). The reaction solution was continuously quenched while stirring with 10.00 g of water in a flask, and then about 40 mL of toluene and about 10 mL of water was added thereto. After separation, 62.99 g of an organic layer containing 5.71 g of benzyl benzoate was obtained (yield: 97%). No crystals precipitated during the reaction, and the reaction solution was a clear solution.

Comparative Example 3 (Batch Method)

In a flask, 1.00 g of benzyl alcohol, 7.60 g of toluene, and 1.22 g of triethylamine were placed, and the inner temperature was adjusted to 0° C. while stirring. Thereafter, 1.56 g of benzoyl chloride was slowly added thereto at a rate of keeping the same inner temperature, and after completion of the addition, the resulting mixture was stirred at 0° C. for 1 hour (amine/solvent=16.1/100 (weight ratio)). Subsequently, the reaction solution was quenched by adding 3.33 g of water thereto. After separation, 9.83 g of an organic layer containing 1.92 g of benzyl benzoate was obtained (yield: 98%). A crystal was precipitated during the reaction, and the reaction solution was a slurry.

37

(3) Production of (R)—N-Benzoyl-α-Phenylethylamine

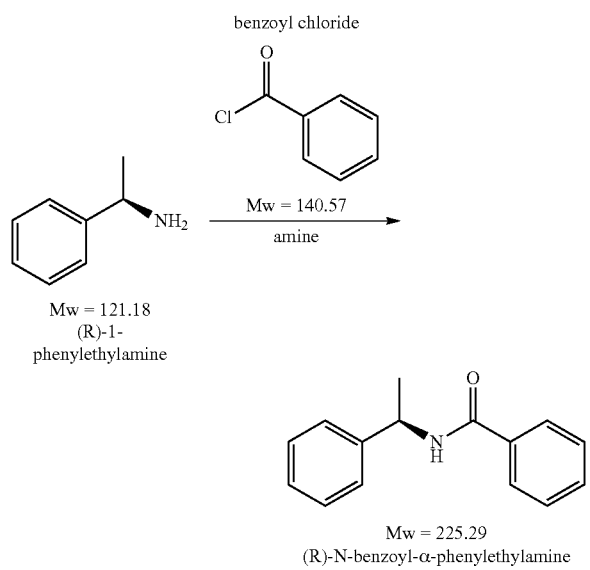

Evaluation Method 3

In the following Examples 7 to 8 and Comparative Example 4, (R)—N-benzoyl-α-phenylethylamine was produced from (R)-1-phenylethylamine and benzoyl chloride. The product was quantified by the HPLC method to calculate the yield. HPLC conditions were as follows.

Column: Zorbax Eclipse Plus C18 (50×4.6 mm, 1.8 μm)
Mobile phase A: 0.1% phosphoric acid aqueous solution
Mobile phase B: acetonitrile
Flow rate: 1.0 ml/min
Detection wavelength: UV 254 nm
Column temperature: 40° C.
Retention time: (R)—N-benzoyl-α-phenylethylamine: 15 minutes
Gradient conditions

| Time (min) | Mobile phase A (%) | Mobile phase B (%) |
|---|---|---|
| 0 | 95 | 5 |
| 3 | 95 | 5 |
| 18 | 45 | 55 |
| 23 | 5 | 95 |

Example 7

To 3.00 g of (R)-1-phenylethylamine, 5.11 g of tetrahydrofuran and 5.97 g of tributylamine were added to prepare a homogeneous solution, and the resulting solution was referred to as solution A. To 4.18 g of benzoyl chloride, 11.53 g of tetrahydrofuran was added to prepare a homogeneous solution, and the resulting solution was referred to as solution B. A T-shape mixer (inner diameter: 2 mm, material: polytetrafluoroethylene (PTFE)) and a retention line (inner diameter of tube: 2 mm, material: polytetrafluoroethylene (PTFE)) were placed in a constant-temperature bath at 0° C. Then, the solution A and the solution B were each transferred using a diaphragm pump (manufactured by KNF Japan Co. Ltd.) at a rate of 2 ml/min and mixed by the T-shape mixer, and the resulting mixture was allowed to flow in the retention line for 1 minute to perform a reaction (amine/solvent=35.9/100 (weight ratio)). The reaction solution was continuously quenched while stirring with 30.00 g of water in a flask, and then 5.58 g of (R)—N-benzoyl-α-phenylethylamine was obtained (yield: 100%). No crystals precipitated during the reaction, and the reaction solution was a clear solution.

38

Example 8

To 3.00 g of (R)-1-phenylethylamine, 5.11 g of tetrahydrofuran and 5.97 g of tributylamine were added to prepare a homogeneous solution, and the resulting solution was referred to as solution A. To 4.18 g of benzoyl chloride, 11.53 g of tetrahydrofuran was added to prepare a homogeneous solution, and the resulting solution was referred to as solution B. A T-shape mixer (inner diameter: 2 mm, material: polytetrafluoroethylene (PTFE)) and a retention line (inner diameter of tube: 2 mm, material: polytetrafluoroethylene (PTFE)) were placed in a constant-temperature bath at 20° C. Then, the solution A and the solution B were each transferred using a diaphragm pump (manufactured by KNF Japan Co. Ltd.) at a rate of 2 ml/min and mixed by the T-shape mixer, and the resulting mixture was allowed to flow in the retention line for 2 minutes to perform a reaction (amine/solvent=35.9/100 (weight ratio)). The reaction solution was continuously quenched while stirring with 30.00 g of water in a flask, and then 5.58 g of (R)—N-benzoyl-α-phenylethylamine was obtained (yield: 100%). No crystals precipitated during the reaction, and the reaction solution was a clear solution.

Comparative Example 4 (Batch Method)

In a flask, 0.50 g of (R)-1-phenylethylamine, 2.50 g of tetrahydrofuran, and 0.54 g of triethylamine were placed, and the inner temperature was adjusted to 0° C. while stirring. Thereafter, 0.70 g of benzoyl chloride was slowly added thereto at a rate of keeping the same inner temperature, and after completion of the addition, the resulting mixture was stirred at 0° C. for 1 hour (amine/solvent=21.6/100 (weight ratio)). Subsequently, the reaction solution was quenched by adding 5.00 g of water thereto. After separation, 2.43 g of an organic layer containing 0.93 g of (R)—N-benzoyl-α-phenylethylamine was obtained (yield: 100%). A crystal was precipitated during the reaction, and the reaction solution was a slurry.

(4) Production of N-[1-(S)-ethoxycarbonyl-3-phenylpropyl]-L-alanyl-N-carboxylic acid anhydride

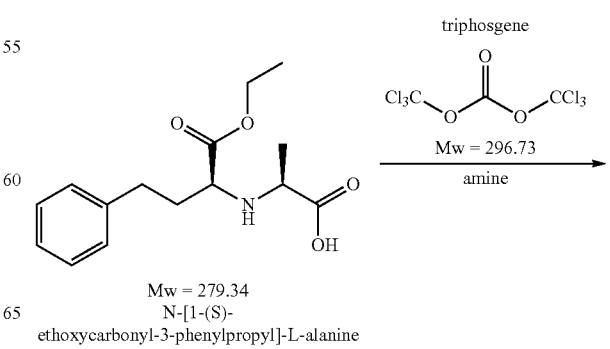

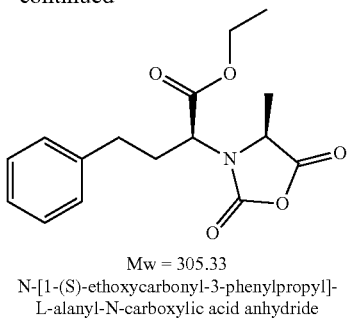

Mw = 305.33
N-[1-(S)-ethoxycarbonyl-3-phenylpropyl]-
L-alanyl-N-carboxylic acid anhydride Evaluation Method 4

In the following Examples 9 to 11, N-[1-(S)-ethoxycarbonyl-3-phenylpropyl]-L-alanyl-N-carboxylic acid anhydride was produced from N-[1-(S)-ethoxycarbonyl-3-phenylpropyl]-L-alanine and triphosgene. The product was quantified by the HPLC method to calculate the yield. HPLC conditions were as follows.

Column: CHIRALPAC IA (250×4.6 mm)
Mobile phase: hexane/ethanol=85/15
Flow rate: 0.8 ml/min
Detection wavelength: UV 254 nm
Column temperature: 30° C.
Retention time: N-[1-(S)-ethoxycarbonyl-3-phenylpropyl]-L-alanyl-N-carboxylic acid anhydride: 12 minutes

Example 9

To 1.50 g of N-[1-(S)-ethoxycarbonyl-3-phenylpropyl]-L-alanine, 13.50 g of tetrahydrofuran and 1.09 g of tributylamine were added to prepare a homogeneous solution, and the resulting solution was referred to as solution A. To 0.64 g of triphosgene, 15.50 g of toluene was added to prepare a homogeneous solution, and the resulting solution was referred to as solution B. A T-shape mixer (inner diameter: 2 mm, material: polytetrafluoroethylene (PTFE)) and a retention line (inner diameter of tube: 2 mm, material: polytetrafluoroethylene (PTFE)) were placed in a constant-temperature bath at 60° C. Then, the solution A and the solution B were each transferred using a diaphragm pump (manufactured by KNF Japan Co. Ltd.) at a rate of 2 ml/min and mixed by the T-shape mixer, and the resulting mixture was allowed to flow in the retention line for 3 minutes to perform a reaction (amine/solvent=3.8/100 (weight ratio)). The reaction solution was continuously quenched while stirring with 75.00 g of a 18% phosphoric acid aqueous solution in a flask. After separation, 40.21 g of an organic layer containing 1.25 g of N-[1-(S)-ethoxycarbonyl-3-phenylpropyl]-L-alanyl-N-carboxylic acid anhydride was obtained (yield: 76%). No crystals precipitated during the reaction, and the reaction solution was a clear solution.

Example 10

To 1.50 g of N-[1-(S)-ethoxycarbonyl-3-phenylpropyl]-L-alanine, 13.50 g of tetrahydrofuran and 1.09 g of tributylamine were added to prepare a homogeneous solution, and the resulting solution was referred to as solution A. To 0.64 g of triphosgene, 15.50 g of toluene was added to prepare a homogeneous solution, and the resulting solution was referred to as solution B. A T-shape mixer (inner diameter: 2 mm, material: polytetrafluoroethylene (PTFE)) and a retention line (inner diameter of tube: 2 mm, material: polytetrafluoroethylene (PTFE)) were placed in a constant-temperature bath at 60° C. Then, the solution A and the solution B were each transferred using a diaphragm pump (manufactured by KNF Japan Co. Ltd.) at a rate of 2 ml/min and mixed by the T-shape mixer, and the resulting mixture was allowed to flow in the retention line for 4 minutes to perform a reaction (amine/solvent=3.8/100 (weight ratio)). The reaction solution was continuously quenched while stirring with 75.00 g of an 18% phosphoric acid aqueous solution in a flask. After separation, 46.59 g of an organic layer containing 1.25 g of N-[1-(S)-ethoxycarbonyl-3-phenylpropyl]-L-alanyl-N-carboxylic acid anhydride was obtained (yield: 76%). No crystals precipitated during the reaction, and the reaction solution was a clear solution.

Example 11

To 1.50 g of N-[1-(S)-ethoxycarbonyl-3-phenylpropyl]-L-alanine, 13.50 g of tetrahydrofuran and 1.09 g of tributylamine were added to prepare a homogeneous solution, and the resulting solution was referred to as solution A. To 0.64 g of triphosgene, 15.50 g of toluene was added to prepare a homogeneous solution, and the resulting solution was referred to as solution B. A T-shape mixer (inner diameter: 2 mm, material: polytetrafluoroethylene (PTFE)) and a retention line (inner diameter of tube: 2 mm, material: polytetrafluoroethylene (PTFE)) were placed in a constant-temperature bath at 35° C. Then, the solution A and the solution B were each transferred using a diaphragm pump (manufactured by KNF Japan Co. Ltd.) at a rate of 2 ml/min and mixed by the T-shape mixer, and the resulting mixture was allowed to flow in the retention line for 4 minutes to perform a reaction (amine/solvent=3.8/100 (weight ratio)). The reaction solution was continuously quenched while stirring with 75.00 g of an 18% phosphoric acid aqueous solution in a flask. After separation, 45.00 g of an organic layer containing 1.13 g of N-[1-(S)-ethoxycarbonyl-3-phenylpropyl]-L-alanyl-N-carboxylic acid anhydride was obtained (yield: 69%). No crystals precipitated during the reaction, and the reaction solution was a clear solution.

(5) Production of Benzyl 4-({[(2S,5R)-6-(benzyloxy)-7-oxo-1,6-diazabicyclo[3.2.1.]oct-2-yl]carbamoyl}amino)piperidine-1-carboxylate

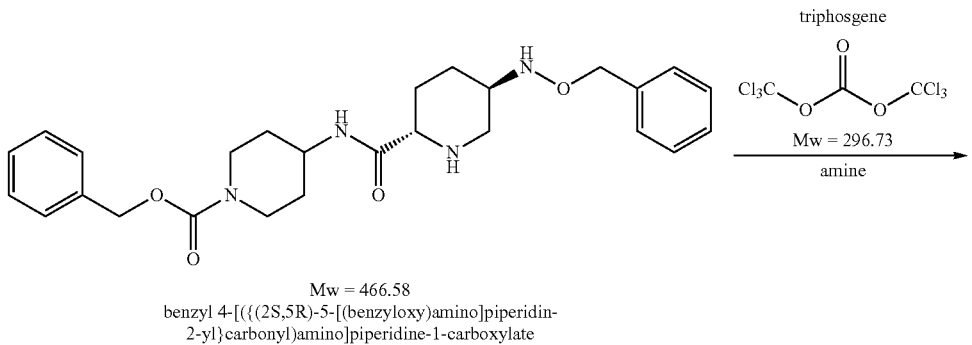

Mw = 466.58
benzyl 4-[({(2S,5R)-5-[(benzyloxy)amino]piperidin-2-yl}carbonyl)amino]piperidine-1-carboxylate

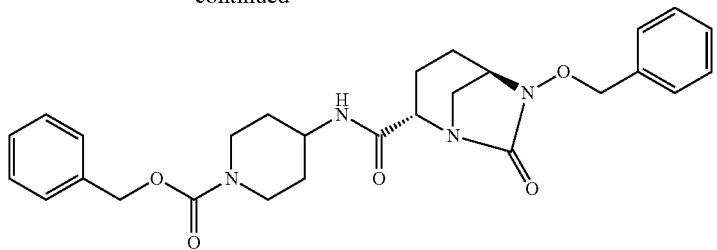

Mw = 492.58
benzyl 4-({[(2S,5R)-6-(benzyloxy)-7-oxo-1,6-diazabicyclo[3.2.1.]oct-2-yl]carbamoyl}amino)piperidine-1-carboxylate Evaluation Method 5

In the following Examples 12 to 14, benzyl 4-({[(2S,5R)-6-(benzyloxy)-7-oxo-1,6-diazabicyclo[3.2.1.]oct-2-yl]carbamoyl}amino)piperidine-1-carboxylate was produced from benzyl 4-[({(2S,5R)-5-[(benzyloxy)amino]piperidin-2-yl}carbonyl)amino]piperidine-1-carboxylate and triphosgene. The product was quantified by the HPLC method to calculate the yield. HPLC conditions were as follows.

Column: Zorbax Eclipse Plus C18 (50×4.6 mm, 1.8 µm)
Mobile phase A: 0.1% phosphoric acid aqueous solution
Mobile phase B: acetonitrile
Flow rate: 1.0 ml/min
Detection wavelength: UV 210 nm
Column temperature: 40° C.
Retention time: benzyl 4-({[(2S,5R)-6-(benzyloxy)-7-oxo-1,6-diazabicyclo[3.2.1.]oct-2-yl]carbamoyl}amino)piperidine-1-carboxylate: 9 minutes
Gradient conditions

| Time (min) | Mobile phase A (%) | Mobile phase B (%) |
|---|---|---|
| 0 | 95 | 5 |
| 15 | 5 | 95 |

Example 12

To 250 mg of benzyl 4-[({(2S,5R)-5-[(benzyloxy)amino]piperidin-2-yl}carbonyl)amino]piperidine-1-carboxylate, 2.53 g of tetrahydrofuran and 317.9 mg of tributylamine were added to prepare a homogeneous solution, and the resulting solution was referred to as solution A. To 127.2 mg of triphosgene, 2.97 g of tetrahydrofuran was added to prepare a homogeneous solution, and the resulting solution was referred to as solution B. A T-shape mixer (inner diameter: 2 mm, material: polytetrafluoroethylene (PTFE)) and a retention line (inner diameter of tube: 2 mm, material: polytetrafluoroethylene (PTFE)) were placed in a constant-temperature bath at 25° C. Then, the solution A and the solution B were each transferred using a syringe pump (manufactured by YMC Co. Ltd.) at a rate of 2 ml/min and mixed by the T-shape mixer, and the resulting mixture was allowed to flow in the retention line for 2 minutes to perform a reaction (amine/solvent=5.8/100 (weight ratio)). The reaction solution was continuously quenched while stirring with a mixed solution of 1.56 g of an 13% phosphoric acid aqueous solution and 4.00 g of toluene in a flask, and then 212 mg of benzyl 4-({[(2S,5R)-6-(benzyloxy)-7-oxo-1,6-diazabicyclo[3.2.1.]oct-2-yl]carbamoyl}amino)piperidine-1-carboxylate was obtained (yield: 80%). No crystals precipitated during the reaction, and the reaction solution was a clear solution.

Example 13

To 250 mg of benzyl 4-[({(2S,5R)-5-[(benzyloxy)amino]piperidin-2-yl}carbonyl)amino]piperidine-1-carboxylate, 2.53 g of tetrahydrofuran and 317.9 mg of tributylamine were added to prepare a homogeneous solution, and the resulting solution was referred to as solution A. To 127.2 mg of triphosgene, 2.97 g of tetrahydrofuran was added to prepare a homogeneous solution, and the resulting solution was referred to as solution B. A T-shape mixer (inner diameter: 2 mm, material: polytetrafluoroethylene (PTFE)) and a retention line (inner diameter of tube: 2 mm, material: polytetrafluoroethylene (PTFE)) were placed in a constant-temperature bath at 0° C. Then, the solution A and the solution B were each transferred using a syringe pump (manufactured by YMC Co. Ltd.) at a rate of 2 ml/min and mixed by the T-shape mixer, and the resulting mixture was allowed to flow in the retention line for 2 minutes to perform a reaction (amine/solvent=5.8/100 (weight ratio)). The reaction solution was continuously quenched while stirring with a mixed solution of 1.56 g of an 13% phosphoric acid aqueous solution and 4.00 g of toluene in a flask, and then 224 mg of benzyl 4-({[(2S,5R)-6-(benzyloxy)-7-oxo-1,6-diazabicyclo[3.2.1.]oct-2-yl]carbamoyl}amino)piperidine-1-carboxylate was obtained (yield: 85%). No crystals precipitated during the reaction, and the reaction solution was a clear solution.

Example 14

To 250 mg of benzyl 4-[({(2S,5R)-5-[(benzyloxy)amino]piperidin-2-yl}carbonyl)amino]piperidine-1-carboxylate, 2.53 g of tetrahydrofuran and 317.9 mg of tributylamine were added to prepare a homogeneous solution, and the resulting solution was referred to as solution A. To 127.2 mg of triphosgene, 2.97 g of tetrahydrofuran was added to prepare a homogeneous solution, and the resulting solution was referred to as solution B. A T-shape mixer (inner diameter: 2 mm, material: polytetrafluoroethylene (PTFE)) and a retention line (inner diameter of tube: 2 mm, material: polytetrafluoroethylene (PTFE)) were placed in a constant-temperature bath at 25° C. Then, the solution A and the solution B were each transferred using a syringe pump (manufactured by YMC Co. Ltd.) at a rate of 2 ml/min and mixed by the T-shape mixer, and the resulting mixture was allowed to flow in the retention line for 8 minutes to perform a reaction (amine/solvent=5.8/100 (weight ratio)). The reaction solution was continuously quenched while stirring with a mixed solution of 1.56 g of an 13% phosphoric acid aqueous solution and 4.00 g of toluene in a flask, and then 190 mg of benzyl 4-({[(2S,5R)-6-(benzyloxy)-7-oxo-1,6-diazabicyclo[3.2.1.]oct-2-yl]carbamoyl}amino)piperidine-1-carboxylate was obtained (yield: 72%). No crystals precipitated during the reaction, and the reaction solution was a clear solution.

(6) Production of (S)-1-phenyl-1,2,3,4-tetrahydroisoquinolinecarbonyl chloride

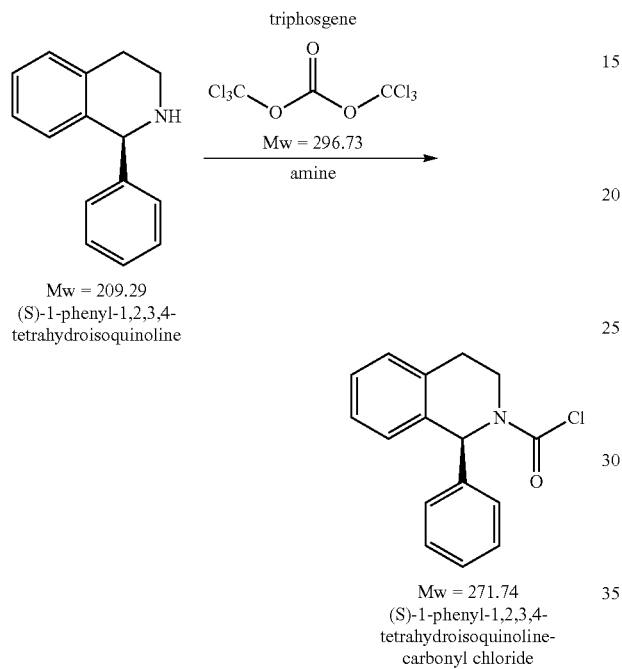

Evaluation Method 6

In the following Example 15, (S)-1-phenyl-1,2,3,4-tetrahydroisoquinolinecarbonyl chloride was produced from (S)-1-phenyl-1,2,3,4-tetrahydroisoquinoline and triphosgene. The product was quantified by the HPLC method to calculate the yield. HPLC conditions were as follows.

Column: CHIRALCEL OD-H (250×4.6 mm)
Mobile phase: hexane/isopropyl alcohol=98/2
Flow rate: 0.7 ml/min
Detection wavelength: UV 220 nm
Column temperature: 35° C.
Retention time: (S)-1-phenyl-1,2,3,4-tetrahydroisoquinolinecarbonyl chloride: 10.5 minutes Example 15

To 2.00 g of (S)-1-phenyl-1,2,3,4-tetrahydroisoquinoline, 10.25 g of toluene and 5.31 g of tributylamine were added to prepare a homogeneous solution, and the resulting solution was referred to as solution A. To 2.27 g of triphosgene, 16.55 g of toluene was added to prepare a homogeneous solution, and the resulting solution was referred to as solution B. A T-shape mixer (inner diameter: 2 mm, material: polytetrafluoroethylene (PTFE)) and a retention line (inner diameter of tube: 2 mm, material: polytetrafluoroethylene (PTFE)) were placed in a constant-temperature bath at 10° C. Then, the solution A and the solution B were each transferred using a syringe pump (manufactured by YMC Co. Ltd.) at a rate of 2.0 ml/min and mixed by the mixer, and the resulting mixture was allowed to flow in the retention line for 2 minutes to perform a reaction (amine/solvent=19.8/100 (weight ratio)). The reaction solution was continuously quenched while stirring with 40 g of 2N hydrochloric acid in a flask. After separation, 38.04 g of an organic layer containing 1.64 g of (S)-1-phenyl-1,2,3,4-tetrahydroisoquinolinecarbonyl chloride was obtained (yield: 63%). No crystals precipitated during the reaction, and the reaction solution was a clear solution.

The invention claimed is:

1. A process for producing an organic compound, comprising:

supplying a reaction substrate, a chlorine-containing compound, a trialkyl amine having 9 to 40 carbon atoms, and an organic solvent, to a flow reactor; and reacting the reaction substrate and the chlorine-containing compound with each other to obtain the organic compound, wherein the reaction substrate has an amino group as a functional group which is capable of reacting with chlorine, and the chlorine-containing compound is at least one selected from the group consisting of compounds of the formula (1) to (8) and triphosgene:

(1)

(2)

(3)

(4)

(5)

(6)

(7)

(8)

wherein $R^1$, $R^2$, and $R^3$ may be the same or different, and each represent an alkyl group having 1 to 20 carbon atoms, an alkyl group having 1 to 20 carbon atoms having a substituent, an alkenyl group having 2 to 20 carbon atoms, an alkenyl group having 2 to 20 carbon atoms having a substituent, a cycloalkyl group having 3 to 20 carbon atoms, a cycloalkyl group having 3 to 20 carbon atoms having a substituent, an aralkyl group having 7 to 20 carbon atoms, an aralkyl group having 7 to 20 carbon atoms having a substituent, an aryl group having 6 to 20 carbon atoms, an aryl group having 6 to 20 carbon atoms having a substituent, a heteroaryl group having 3 to 20 carbon atoms, or a heteroaryl group having 3 to 20 carbon atoms having a substituent; and $R^1$ and $R^2$, $R^1$ and $R^3$, and $R^2$ and $R^3$ may be bonded to each other.

2. The process according to claim 1, wherein
the flow reactor has two or more raw material feeding ports, a mixing unit configured to mix a raw material fed from the feeding ports, and a reactor unit configured to flow a mixed solution therein, and a first organic solvent solution comprising the reaction substrate and the trialkyl amine dissolved therein, and a second organic solvent solution comprising the chlorine-containing compound dissolved therein, are fed to the reactor unit from different raw material feeding ports.

3. The process according to claim 1, wherein the organic solvent is at least one selected from the group consisting of an aliphatic hydrocarbon solvent, an aromatic hydrocarbon solvent, an ether solvent, an ester solvent, a ketone solvent, a nitrile solvent, and an amide solvent.

4. The process according to claim 1, wherein the trialkyl amine and the organic solvent are supplied to the flow reactor such that an amount of the trialkyl amine is 3 parts by weight or more with respect to 100 parts by weight of the organic solvent.

5. The process according to claim 1, wherein the trialkyl amine is tripropylamine, tributylamine, trihexylamine, or trioctylamine.

6. The process according to claim 1, wherein
the reaction substrate is at least one selected from the group consisting of compounds of the formulae (a1) and (a3):

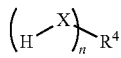

(a1)

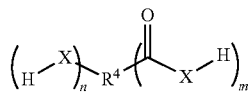

(a3)

wherein
the compounds of the formulae (a1) and (a3) each have at least one amino group;
$R^4$ represents an alkyl group (1) having 1 to 20 carbon atoms, an alkyl group (2) having 1 to 20 carbon atoms having a substituent, a divalent or trivalent group obtained by removing one or two hydrogen atoms from the alkyl group (1) or the alkyl group (2), an alkenyl group (1) having 2 to 20 carbon atoms, an alkenyl group (2) having 2 to 20 carbon atoms having a substituent, a divalent or trivalent group obtained by removing one or two hydrogen atoms from the alkenyl group (1) or the alkenyl group (2), a cycloalkyl group (1) having 3 to 20 carbon atoms, a cycloalkyl group (2) having 3 to 20 carbon atoms having a substituent, a divalent or trivalent group obtained by removing one or two hydrogen atoms from the cycloalkyl group (1) or the cycloalkyl group (2), an aralkyl group (1) having 7 to 20 carbon atoms, an aralkyl group (2) having 7 to 20 carbon atoms having a substituent, a divalent or trivalent group obtained by removing one or two hydrogen atoms from the aralkyl group (1) or the aralkyl group (2), an aryl group (1) having 6 to 20 carbon atoms, an aryl group (2) having 6 to 20 carbon atoms having a substituent, a divalent or trivalent group obtained by removing one or two hydrogen atoms from the aryl group (1) or the aryl group (2), a heteroaryl group (1) having 3 to 20 carbon atoms, a heteroaryl group (2) having 3 to 20 carbon atoms having a substituent, or a divalent or trivalent group obtained by removing one or two hydrogen atoms from the heteroaryl group (1) or the heteroaryl group (2);

X represents O or $NR^5$;

$R^5$ represents hydrogen atom, an alkyl group having 1 to 20 carbon atoms, an alkyl group having 1 to 20 carbon atoms having a substituent, an alkenyl group having 2 to 20 carbon atoms, an alkenyl group having 2 to 20 carbon atoms having a substituent, a cycloalkyl group having 3 to 20 carbon atoms, a cycloalkyl group having 3 to 20 carbon atoms having a substituent, an aralkyl group having 7 to 20 carbon atoms, an aralkyl group having 7 to 20 carbon atoms having a substituent, an aryl group having 6 to 20 carbon atoms, an aryl group having 6 to 20 carbon atoms having a substituent, a heteroaryl group having 3 to 20 carbon atoms a heteroaryl group having 3 to 20 carbon atoms having a substituent, an alkoxy group having 1 to 20 carbon atoms, an alkoxy group having 1 to 20 carbon atoms having a substituent, an aralkyloxy group having 7 to 20 carbon atoms, an aralkyloxy group having 7 to 20 carbon atoms having a substituent, an aryloxy group having 6 to 20 carbon atoms, an aryloxy group having 6 to 20 carbon atoms having a substituent;

$R^4$ and $R^5$ may be bonded to each other; when a plurality of X's are present, X's may be the same or different; and n and m each represent an integer of 1 to 3, and
the organic compound obtained by reacting the reaction substrate and the chlorine-containing compound is at least one selected from the group consisting of compounds having the formulae (9) to (17) and (26) to (34):

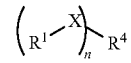

(9)

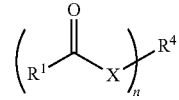

(10)

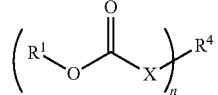

(11)

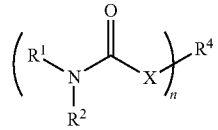

(12)

(13) 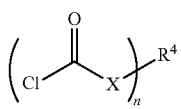

(14) 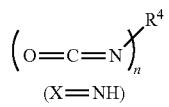
(X=NH)

(15) 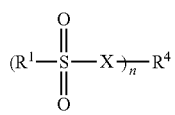

(16) 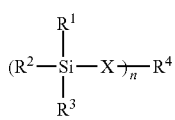

(17) 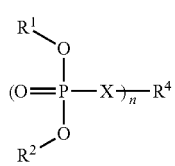

(26) 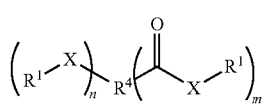

(27) 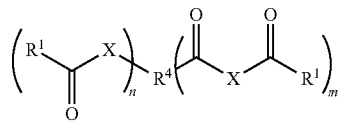

(28) 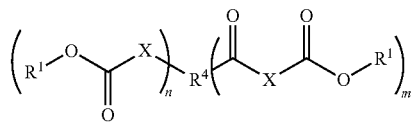

(29) 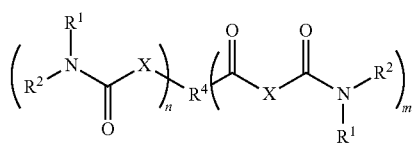

(30) 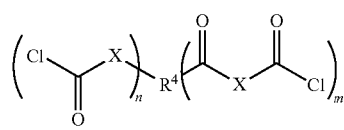

(31) 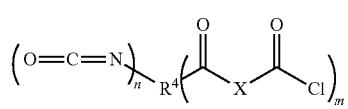

(32) 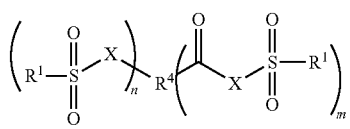

(33) 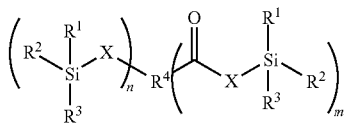

(34) 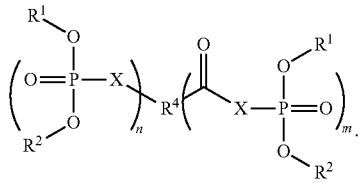

7. The process according to claim 6, wherein the reaction substrate is (S)-1-phenyl-1,2,3,4-tetrahydroisoquinoline, the chlorine-containing compound is phosgene (5) or triphosgene, and the organic compound obtained by reacting the reaction substrate and the chlorine-containing compound is (S)-1-phenyl-1,2,3,4-tetrahydroisoquinolinecarbonyl chloride.

8. The process according to claim 1, wherein
the reaction substrate is at least one selected from the group consisting of compounds of the formulae (a4) to (a6):

(a4) 

(a5) 

(a6) 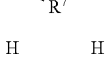

wherein the compounds of the formulae (a4) to (a6) each have at least one amino group;
$R^6$ represents an alkyl group having 1 to 20 carbon atoms, an alkyl group having 1 to 20 carbon atoms having a substituent, an alkenyl group having 2 to 20 carbon atoms, an alkenyl group having 2 to 20 carbon atoms having a substituent, a cycloalkyl group having 3 to 20 carbon atoms, a cycloalkyl group having 3 to 20 carbon atoms having a substituent, an aralkyl group having 7 to 20 carbon atoms, an aralkyl group having 7 to 20 carbon atoms having a substituent, an aryl group having 6 to 20 carbon atoms, an aryl group having 6 to 20 carbon atoms having a substituent, a heteroaryl group having 3 to 20 carbon atoms, or a heteroaryl group having 3 to 20 carbon atoms having a substituent;
$R^7$ and $R^8$ each represent an alkylene group having 1 to 10 carbon atoms or an alkylene group having 1 to 10 carbon atoms having a substituent;
X represents O or $NR^5$;
$R^5$ represents hydrogen atom, an alkyl group having 1 to 20 carbon atoms, an alkyl group having 1 to 20 carbon atoms having a substituent, an alkenyl group having 2 to 20 carbon atoms, an alkenyl group having 2 to 20 carbon atoms having a substituent, a cycloalkyl group having 3 to 20 carbon atoms, a cycloalkyl group having 3 to 20 carbon atoms having a substituent, an aralkyl group having 7 to 20 carbon atoms, an aralkyl group having 7 to 20 carbon atoms having a substituent, an aryl group having 6 to 20 carbon atoms, an aryl group having 6 to 20 carbon atoms having a substituent, a heteroaryl group having 3 to 20 carbon atoms a heteroaryl group having 3 to 20 carbon atoms having a substituent, an alkoxy group having 1 to 20 carbon atoms, an alkoxy group having 1 to 20 carbon atoms having a substituent, an aralkyloxy group having 7 to 20 carbon atoms, an aralkyloxy group having 7 to 20 carbon atoms having a substituent, an aryloxy group having 6 to 20 carbon atoms, or an aryloxy group having 6 to 20 carbon atoms having a substituent;

when a plurality of X's are present, X's may be the same or different, the chlorine-containing compound is phosgene or triphosgene, and the organic compound obtained by reacting the reaction substrate and the chlorine-containing compound is at least one selected from the group consisting of compounds of the formulae (35) to (37):

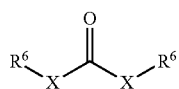
(35)

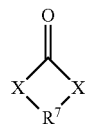
(36)

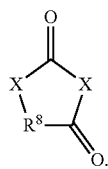
(37)

9. The process according to claim 1, wherein the reaction substrate is N-[1-(S)-ethoxycarbonyl-3-phenylpropyl]-L-alanine, benzyl 4-[({(2 S,5R)-5-[(benzyloxy)amino]piperidin-2-yl}carbonyl)amino]piperidine-1-carboxylate, tert-butyl 4-[({(2S,5R)-5-[(benzyloxy)amino]piperidin-2-yl}carbonyl)amino]piperidine-1-carboxylate, benzyl (2S,5R)-5-benzyloxyamino-piperidine-2-carboxylate, methyl (2S,5R)-5-benzyloxyamino-piperidine-2-carboxylate, or (2S,5R)-5-benzyloxyamino-piperidine-2-carboxamide, the chlorine-containing compound is phosgene or triphosgene, and the organic compound obtained by reacting the reaction substrate and the chlorine-containing compound is N-[1-(S)-ethoxycarbonyl-3-phenylpropyl]-L-alanyl-N-carboxylic acid anhydride, benzyl 4-({[(2S,5R)-6-(benzyloxy)-7-oxo-1,6-diazabicyclo[3.2.1]oct-2-yl]carbamoyl}amino)piperidine-1-carboxylate, tert-butyl 4-({[(2S,5R)-6-(benzyloxy)-7-oxo-1,6-diazabicyclo[3.2.1]oct-2-yl]carbamoyl}amino)piperidine-1-carboxylate, benzyl (4R,6S)-3-(benzyloxy)-2-oxo-1,3-diazabicyclo[2,2,1]heptane-6-carboxylate, methyl (4R,6S)-3-(benzyloxy)-2-oxo-1,3-diazabicyclo[2,2,1]heptane-6-carboxylate, or (4R,6S)-3-(benzyloxy)-2-oxo-1,3-diazabicyclo[2,2,1]heptane-6-carboxamide.

10. The process according to claim 1, wherein the reacting is performed at a temperature of from −50° C. to 100° C.

11. The process according to claim 1, wherein in the reacting, an amount of water in the organic solvent is 10 wt % or less.

12. The process according to claim 1, wherein in the reacting, an amount of water in the organic solvent is 1 wt % or less.

13. The process according to claim 1, wherein the trialkyl amine and the reaction substrate are supplied to the flow reactor such that an amount of the trialkyl amine is from 0.1 mol to 15 mol relative to 1 mol of the functional group of the reaction substrate.

14. The process according to claim 1, wherein the trialkyl amine and the chlorine-containing compound are supplied to the flow reactor such that an amount of the trialkyl amine is from 0.2 mol to 4 mol relative to 1 mol of chlorine atoms in the chlorine-containing compound.

* * * * *